(12) United States Patent
Spellman et al.

(10) Patent No.: US 9,506,926 B2
(45) Date of Patent: Nov. 29, 2016

(54) MOLECULAR PREDICTORS OF THERAPEUTIC RESPONSE TO SPECIFIC ANTI-CANCER AGENTS

(75) Inventors: Paul T. Spellman, Portland, OR (US); Joe W. Gray, Lake Oswego, OR (US); Anguraj Sadanandam, Pollachi (IN); Laura M. Heiser, Lake Oswego, OR (US); William J. Gibb, San Anselmo, CA (US); Wen-lin Kuo, Lin-Kou Town (TW); Nicholas J. Wang, Porland, OR (US)

(73) Assignee: The Regents of the University of California, Oakland, CA (US)

( * ) Notice: Subject to any disclaimer, the term of this patent is extended or adjusted under 35 U.S.C. 154(b) by 554 days.

(21) Appl. No.: 13/401,780

(22) Filed: Feb. 21, 2012

(65) Prior Publication Data

US 2012/0214829 A1 Aug. 23, 2012

Related U.S. Application Data

(60) Provisional application No. 61/444,660, filed on Feb. 18, 2011.

(51) Int. Cl.
| | |
|---|---|
| *G01N 33/50* | (2006.01) |
| *G01N 33/574* | (2006.01) |
| *A61K 31/165* | (2006.01) |
| *A61K 31/167* | (2006.01) |
| *A61K 31/437* | (2006.01) |
| *A61K 31/513* | (2006.01) |
| *A61K 31/517* | (2006.01) |
| *C12Q 1/68* | (2006.01) |

(52) U.S. Cl.
CPC ....... *G01N 33/57484* (2013.01); *A61K 31/165* (2013.01); *A61K 31/167* (2013.01); *A61K 31/437* (2013.01); *A61K 31/513* (2013.01); *A61K 31/517* (2013.01); *C12Q 1/6886* (2013.01); *C12Q 2600/106* (2013.01); *C12Q 2600/158* (2013.01); *G01N 2800/52* (2013.01)

(58) Field of Classification Search
None
See application file for complete search history.

(56) References Cited

U.S. PATENT DOCUMENTS

2011/0217297 A1* 9/2011 Kao et al. .................. 424/133.1

OTHER PUBLICATIONS

Yeoh et al., Classification, subtype discovery, and prediction of outcome in pediatric acute lymphoblastic leukemia by gene expression profiling, Mar. 2002, Cancer Cell, vol. 1, issue 2, pp. 133-143.*

* cited by examiner

*Primary Examiner* — Jason Sims
(74) *Attorney, Agent, or Firm* — Michelle Chew Wong; Lawrence Berkeley National Laboratory

(57) ABSTRACT

Herein is described the use of a collection of 50 breast cancer cell lines to match responses to 77 conventional and experimental therapeutic agents with transcriptional, proteomic and genomic subtypes found in primary tumors. Almost all compounds produced strong differential responses across the cell lines produced responses that were associated with transcriptional and proteomic subtypes and produced responses that were associated with recurrent genome copy number abnormalities. These associations can now be incorporated into clinical trials that test subtype markers and clinical responses simultaneously.

2 Claims, 19 Drawing Sheets

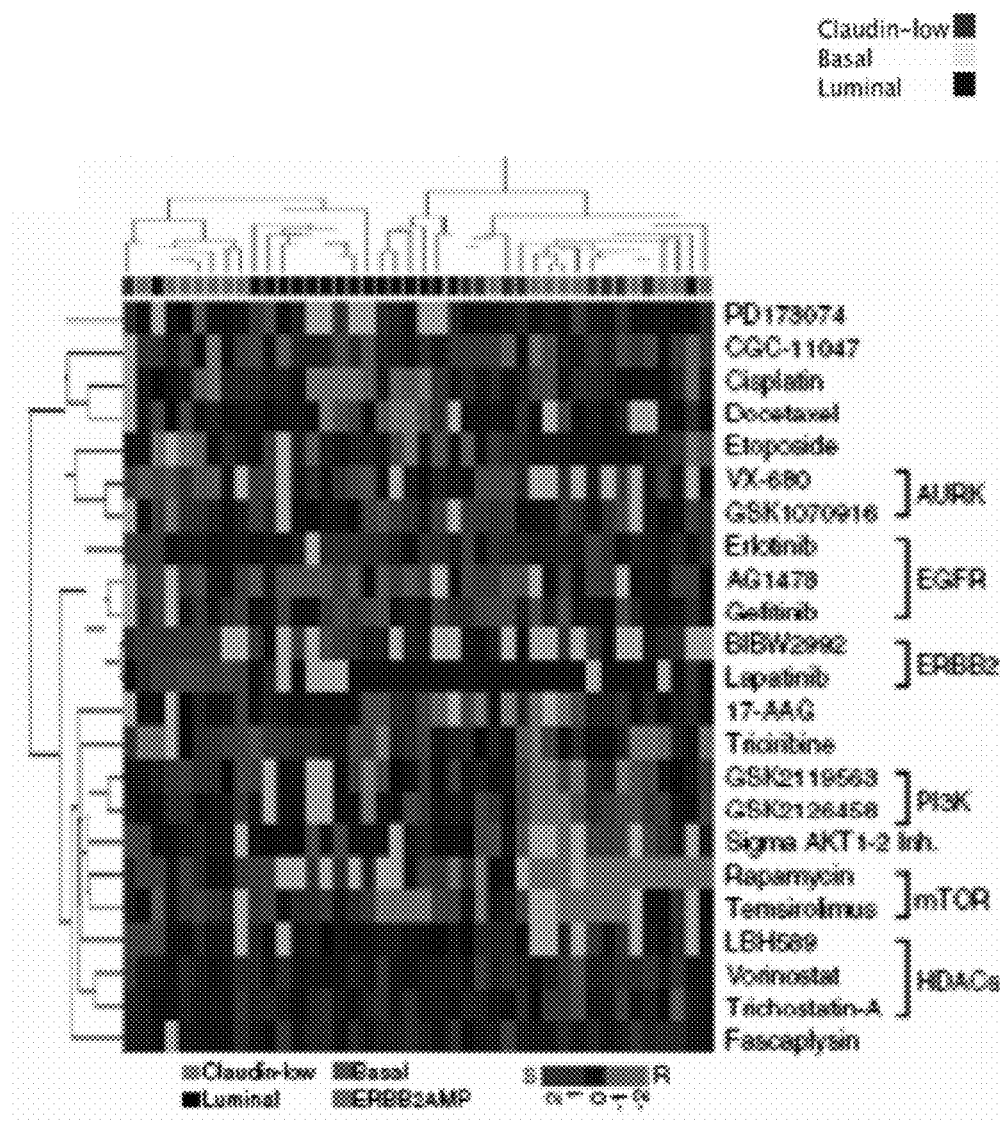

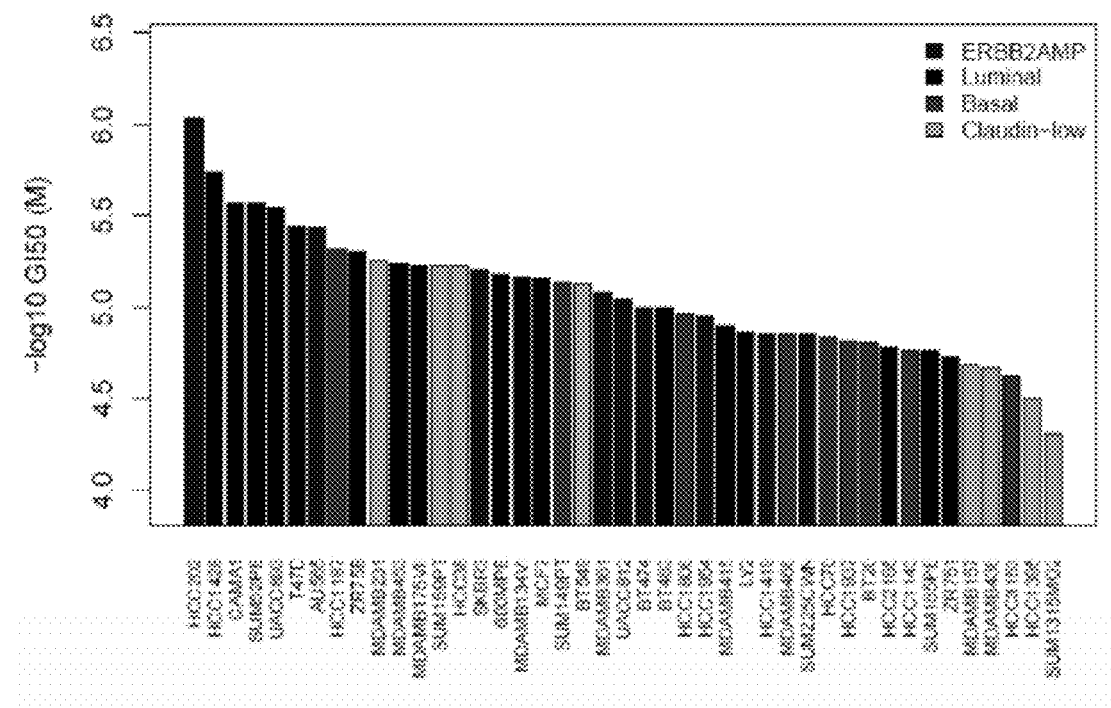

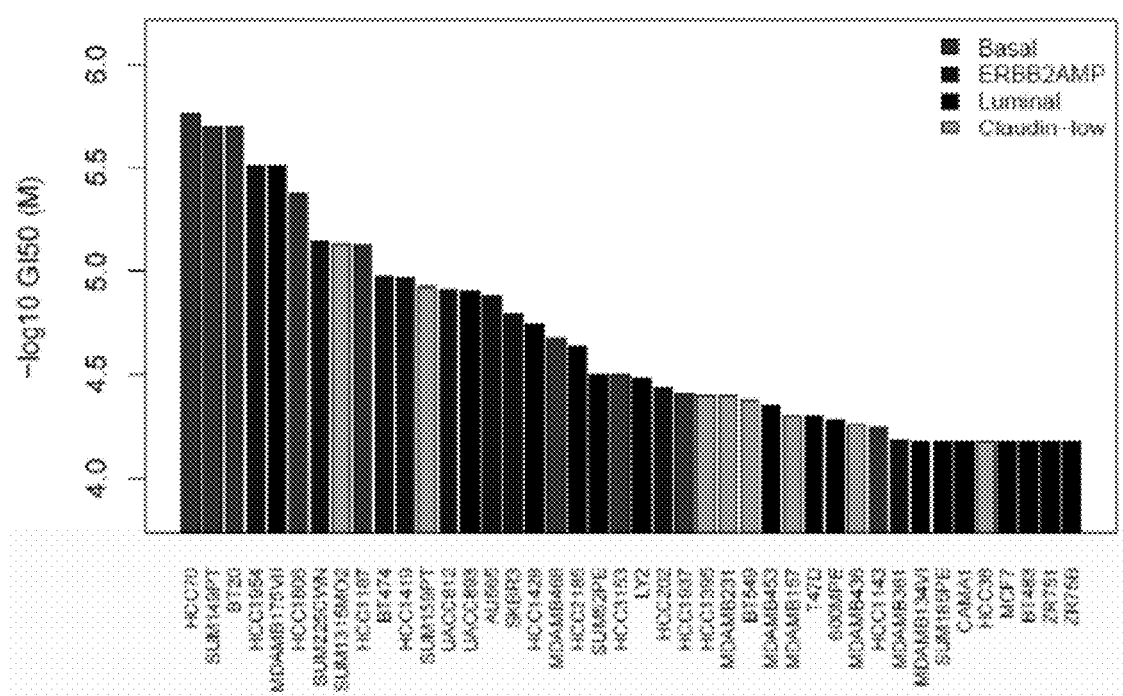

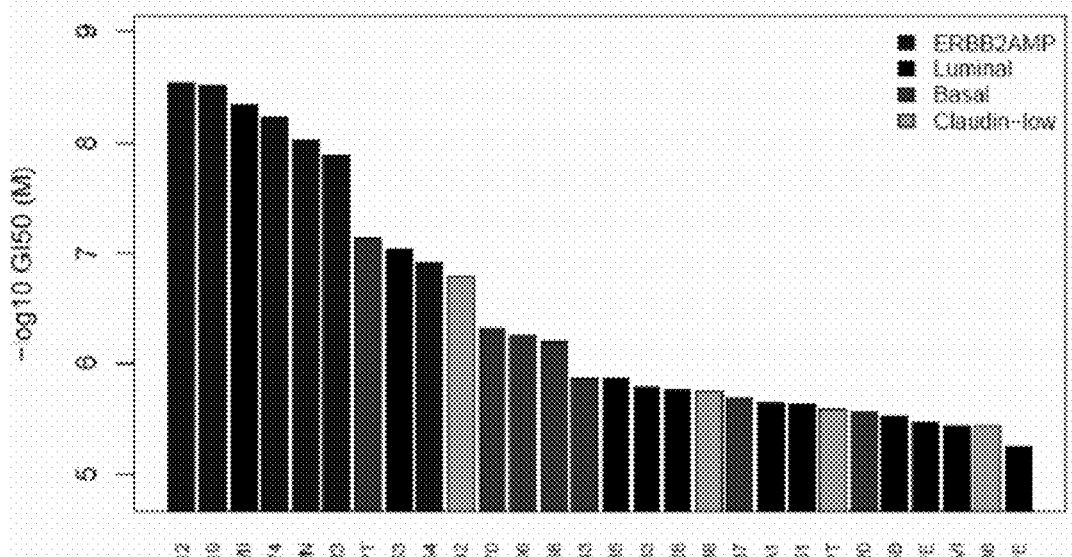

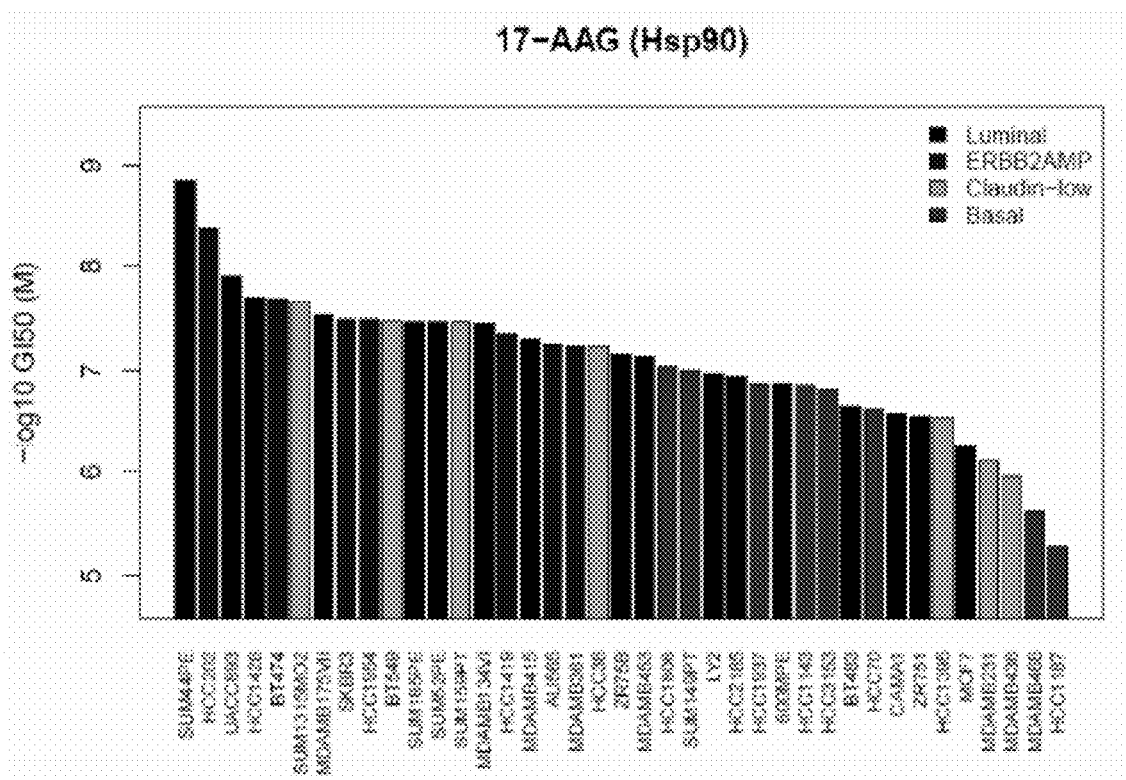

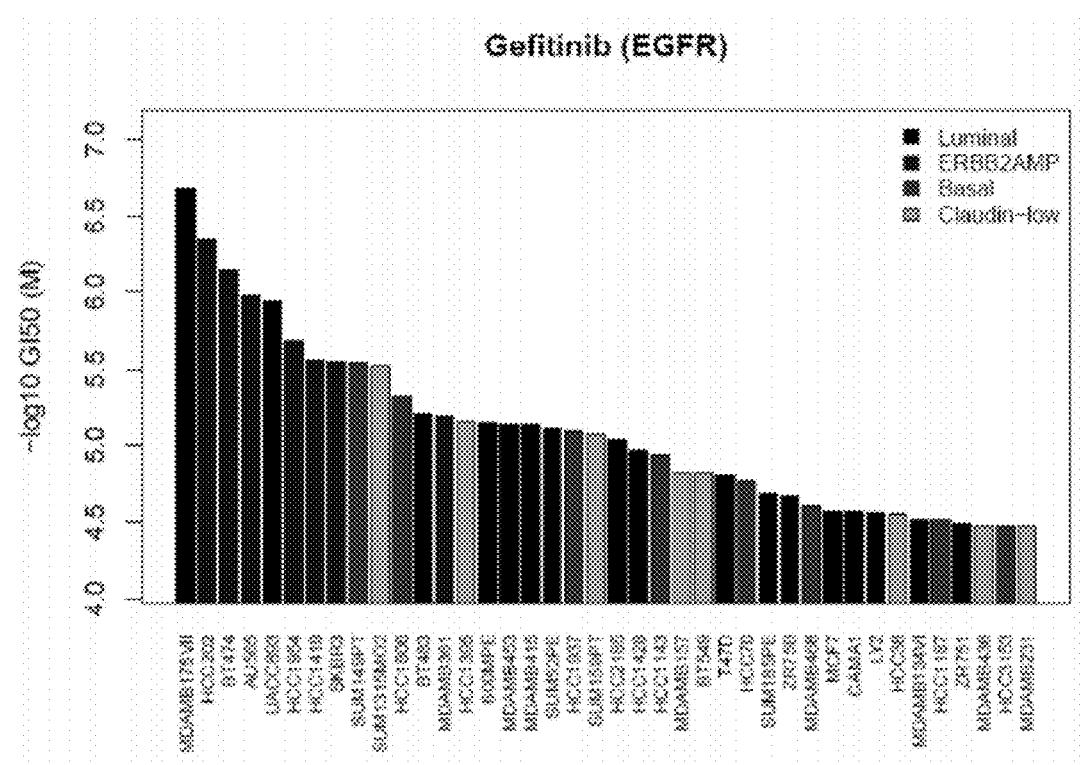

MOLECULAR PREDICTORS OF THERAPEUTIC RESPONSE TO SPECIFIC ANTI-CANCER AGENTS

CROSS-REFERENCE TO RELATED APPLICATIONS

Figure 1A:
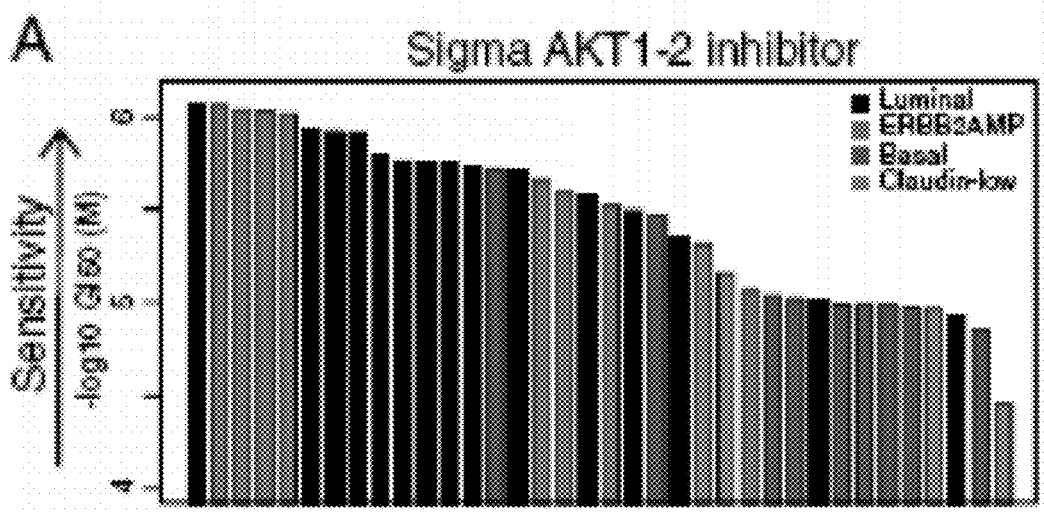

This application claims priority to U.S. Provisional Patent Application No. 61/444,660, filed on Feb. 18, 2011, which is hereby incorporated by reference in its entirety.

This application is related to and hereby incorporates by reference International Patent application no. PCT/US2010/056743, which is hereby incorporated by reference in its entirety.

STATEMENT OF GOVERNMENTAL SUPPORT

This work was supported in part by Contract No. DE-AC02-05CH11231 awarded by the Department of Energy, by Grant Nos. CA058207; U54 CA112970; NHGRI U24, CA126551, and K08CA137153 awarded by the National Cancer Institution of the National Institutes of Health, and by a Work for Others Agreements LB06-002417 with GlaxoSmithKline; LB09005492 with Millennium Pharmaceuticals, Inc.; LB-08004488 with Cytokinetics, Inc.; LB07003395 with Cellgate, Inc. and LB08005005 with Progen Pharmaceuticals Ltd. The government has certain rights in the invention.

BACKGROUND OF THE INVENTION

1. Field of the Invention

The invention relates to the field of biomarkers which are diagnostic or prognostic for predicting patient response to specific anti-cancer compounds and therapeutics.

2. Background

The pharmaceutical industry estimates that there are more than 800 small molecule agents and biologics now under development for treatment of human malignancies (website for newmeds.phrma.org). These agents target numerous molecular features thought to distinguish between tumor and normal cells. These range from broad specificity conventional therapeutics such as anti-metabolites and DNA cross-linking agents that currently serve as mainline breast cancer treatments, to agents that interfere with aspects to a new generation of agents such as trastuzumab that selectively target molecular events and pathways that are deregulated in cancer subsets.

The general trend in drug development today is toward development of more targeted agents because these are expected to show increased efficacy and lower toxicity than conventional agents. Some drugs such as the ERBB2/EGFR inhibitor, lapatinib show high target specificity while others such as the SRC inhibitor, dasatinib, inhibit a broad range of kinases. Given the large number of agents in clinical development, there is growing recognition that clinical trials must include predictors of response and must stratify patients entering the trial.

Unfortunately, the specificity of most drugs is not sufficiently high to allow the subtypes in which the drugs will be effective to be predicted with high confidence. Responsive subsets can be identified during the course of molecular marker based clinical trials however this is logistically difficult, expensive and does not allow experimental compounds to be tested in subpopulations most likely to respond early in the trials process. Indeed, the majority of drugs now under development will never be tested in breast cancer so the probability is high that compounds that are effective only in subpopulations of breast cancer will be missed.

SUMMARY OF THE INVENTION

Personalized medicine promises to deliver specific treatment(s) to patients likely to benefit from them. Herein it is shown that testing therapeutic compounds in a panel of breast cancer cell lines identifies breast cancer subtypes that are likely to respond to approximately 30% of tested compounds. This supports the importance of defining response-related molecular subtypes in breast cancer treatment. It also suggests the utility of preclinical screening of experimental compounds in well-characterized cell line panels to identify candidate response associated molecular signatures that can be used for sensitivity enrichment in early-phase clinical trials.

Thus the invention provides for a method for identifying a cancer patient suitable for treatment with an anti-cancer agent selected from the group of Vorinostat, Trichostatin A, Erlotinib, Fluoruracil and GSK1070916 comprising: (a) measuring the expression level of a target gene in a sample from the patient; and (b) comparing the expression level of said gene from the patient with the expression level of the gene in a normal tissue sample or a reference expression level, wherein an increase or decrease in the expression level of the target gene indicates the patient is suitable for treatment with one of the selected anti-cancer agents.

A method for identifying a cancer patient suitable for treatment, comprising (a) measuring the genomic copy number or expression level of a gene encoding ER and PR in a sample from the patient, and (b) comparing the ER and PR genomic copy numbers in the patient to normal copy number or expression level of the genes encoding ER and PR, the expression level of the genes encoding ER and PR in a normal tissue sample or a reference expression level, or the average expression level of ER and PR in a panel of normal cell lines or cancer cell lines, wherein a positive level or an increase in the expression level of ER and PR indicates the patient is suitable for treatment with vorinostat or trichostatin A.

A method for identifying a cancer patient suitable for treatment, (a) measuring the HER2 protein levels in a sample from the patient, and (b) comparing the ER and PR protein levels from the sample to normal ER and PR protein levels in a normal tissue sample or a reference protein level, or the average protein level of ER and PR in a panel of normal cell lines or cancer cell lines, wherein a positive level or an increase in the protein levels of ER and PR indicates the patient is suitable for treatment with Vorinostat or Trichostatin A.

A method of treating a cancer patient comprising (a) identifying a cancer patient who is suitable for treatment with one of five identified clinical agents, Vorinostat, Trichostatin A, Erlotinib, Fluoruracil or GSK1070916 and (b) administering a therapeutically effective amount of the clinical agent.

A method of treating a cancer patient comprising (a) obtaining a biopsy of a cancer patient and identifying the cellular subtype of the cells in said cancer patient; (b) determining if the subtype is suitable for treatment with one of five identified clinical agents, Vorinostat, Trichostatin A, Erlotinib, Fluoruracil or GSK1070916 and (c) administering a therapeutically effective amount of the clinical agent.

If the subtype is ER+/PR+, then the patient is suitable for treatment with Vorinostat and/or Trichostatin A. If the subtype is luminal, then the patient is suitable for treatment with Vorinostat and/or Trichostatin A. If the subtype is basal, then the patient is suitable for treatment with Erlotinib and/or Fluoruracil. If the subtype is ER-/PR-/HER2-Claudin+, then the patient is suitable for treatment with Erlotinib and/or Fluoruracil. If the subtype is Claudin-low, then the patient is suitable for treatment with GSK1070916 and/or Fluoruracil. If the subtype is KI67+, then the patient is suitable for treatment with Fluorouracil. If the subtype is low or no 20q13 amplification is measured, then the patient is suitable for treatment with GSK1070916.

BRIEF DESCRIPTION OF THE FIGURES AND TABLES

FIG. 1. The cell lines show a broad range of responses to therapeutic compounds. A. Luminal and ERBB2AMP cell lines preferentially respond to AKT inhibition. Each bar represents the response of a single breast cancer cell line to the Sigma AKT1-2 inhibitor, and is colored according to subtype. Cell lines are ordered by decreasing sensitivity ($-\log_{10}(GI_{50})$). B. Drug response profiles for compounds with similar mechanisms and targets are highly correlated. Heatmap shows hierarchical clustering of correlations between responses of breast cancer cell lines treated with one of eight compounds. Red indicates positively correlated sensitivity across the panel of cell lines. Green indicates anti-correlated drug response profiles. C. Hierarchical analysis of quantitative responses across cell lines and compounds. Each column represents one cell line, each row represents median centered $-\log 10(GI_{50})$ for a particular compound. Both rows and columns are hierarchically clustered. Only compounds with a significant subtype effect are included. In the heatmap, red (positive values) represents sensitivity, green (negative values) represents resistance, and gray represents missing values. Colored bars below dendogram indicate sample subtype. Overall, cell lines of similar subtype tend to cluster together, as do compounds with similar targets or mechanisms. D. CNAs are associated with compound response. Boxplots show distribution of response sensitivity for cell lines with aberrant (A) and normal (N) copy number at the noted genomic locus. a. 20q13 (STK15/AURKA) amplification is associated with GSK1070916 (A=7, N=26 samples). b. Amplification at 11q13 (CCND1) is associated with response to carboplatin (A=9, N=28 samples) c. 17q12 (ERBB2) amplification is associated with sensitivity to BIBW2992 (A=6, N=19 samples), 17-AAG (A=7, N=27 samples), gefitinib (A=7, N=18 samples) and resistance to NU6102 (A=6, N=21 samples).

Figure 2A:
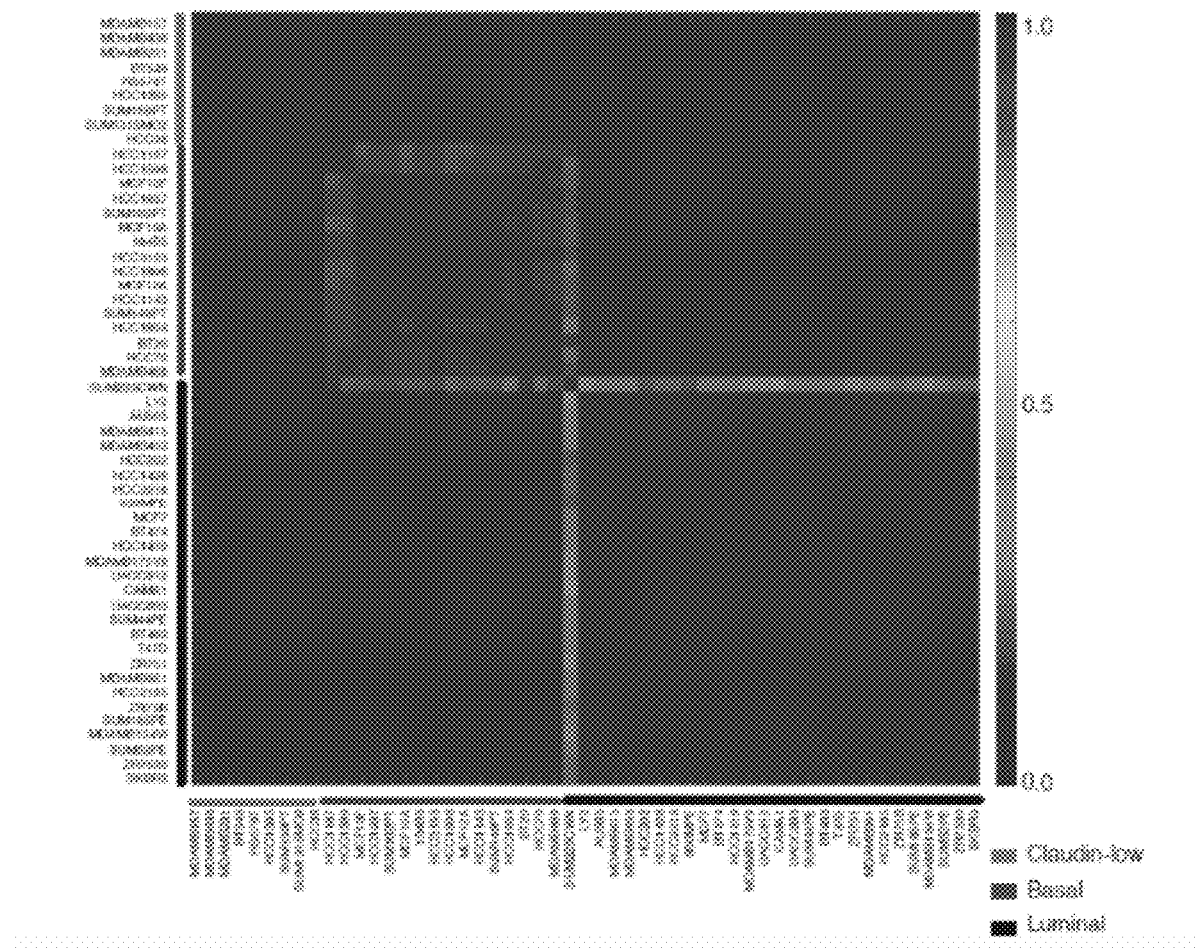
Figure 2B:
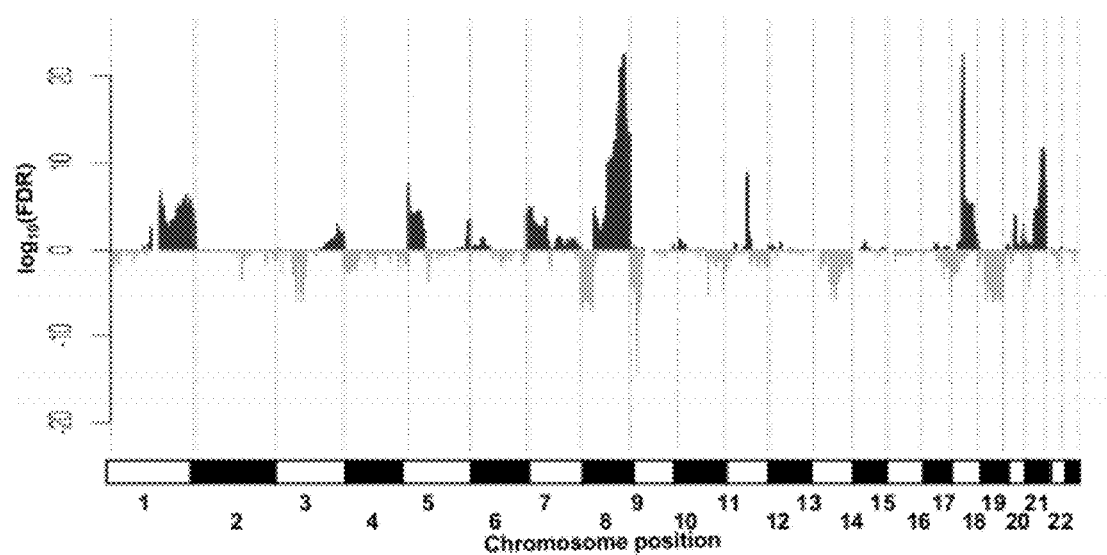

FIG. 2. Genomic and transcriptional profiles of the breast cancer cell lines. A. Hierarchical consensus clustering matrix for 55 breast cancer cell lines showing 3 clusters (claudin-low, luminal, basal) based on gene expression signatures. For each cell line combination, color intensity is proportional to consensus. B. DNA copy number aberrations for 43 breast cancer cell lines are plotted with $\log_{10}(FDR)$ of GISTIC analysis on the y-axis and chromosome position on the x-axis. Copy number gains are shown in red with positive $\log_{10}(FDR)$ and losses are shown in green with negative $\log_{10}(FDR)$.

Figure 3:
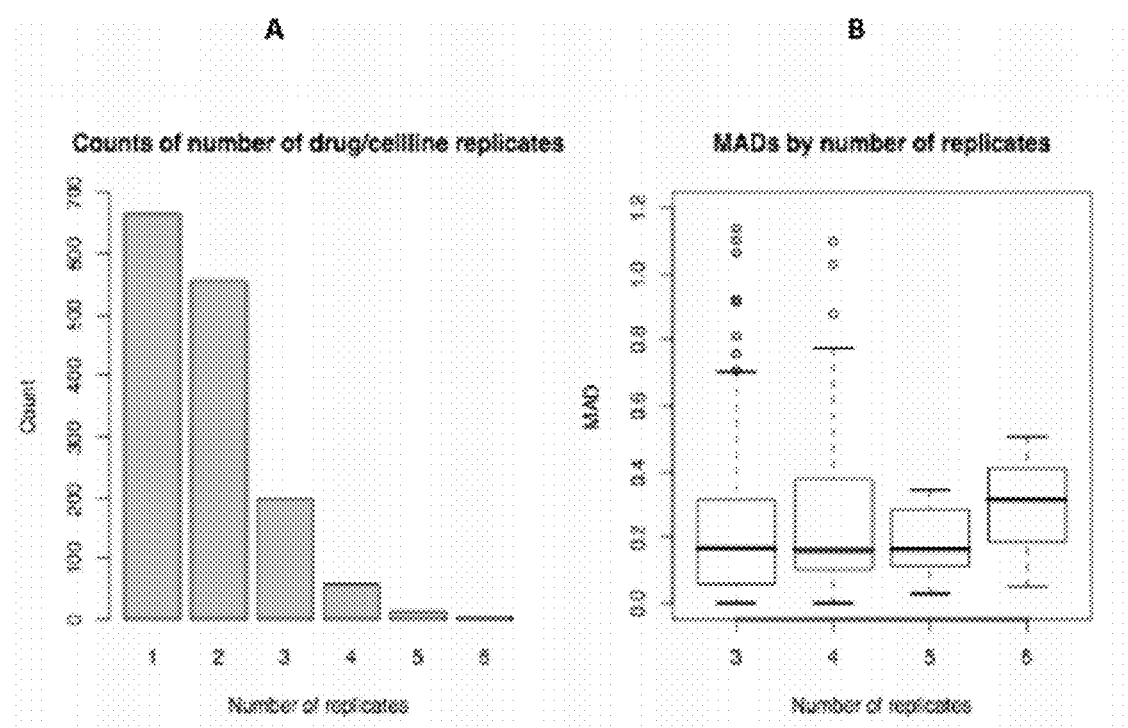
Figure 3:
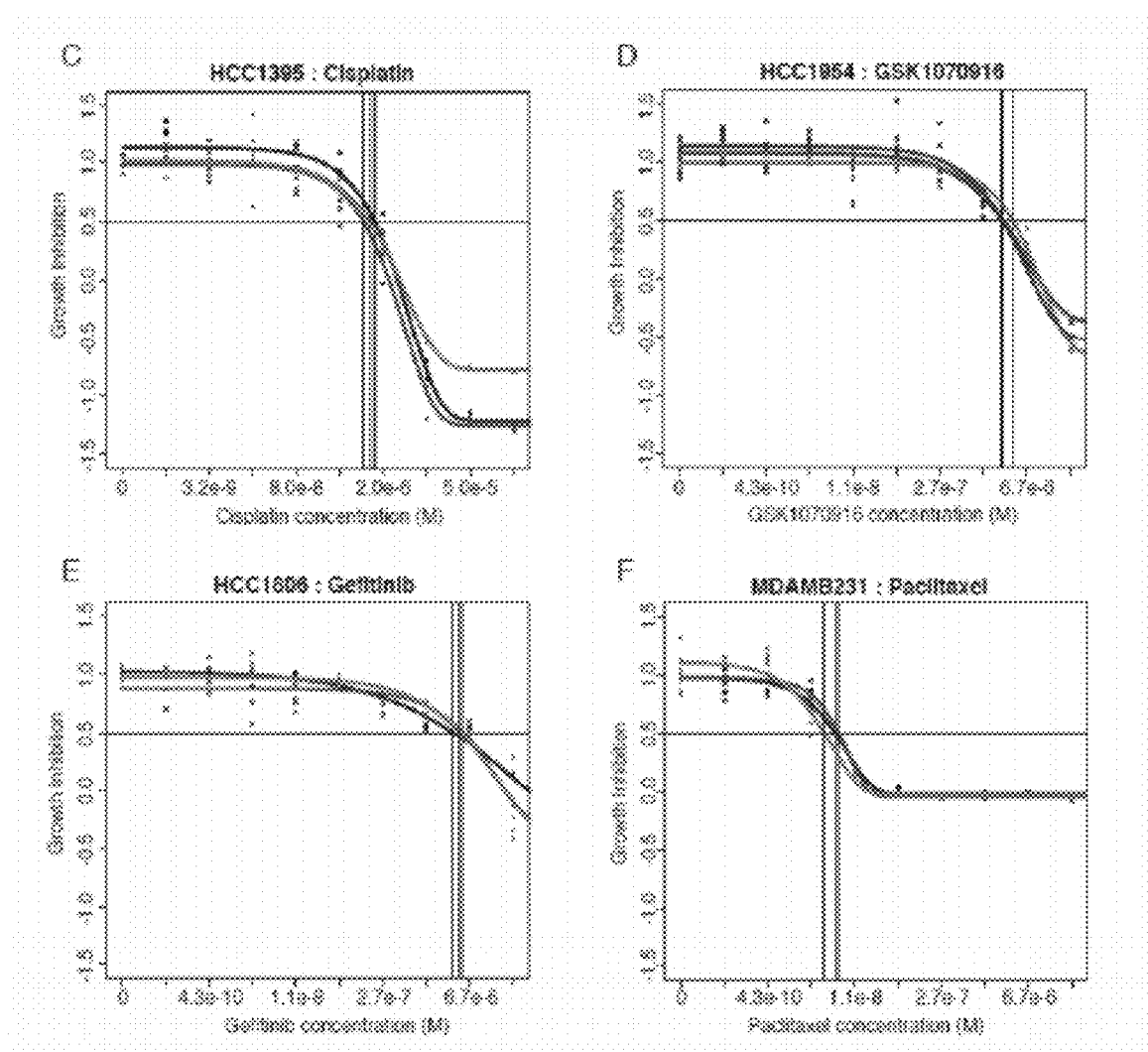

FIG. 3. GI50 calculations are highly reproducible. A. Each bar represents a count of the frequency of replicated drug/cell line combinations. Most cell lines were tested only one time against a particular compound, but some drug/cell line combinations were tested multiple times. B. Each boxplot represents the distribution of median absolute deviations for drug/cell line pairs with 3 or 4 replicates. C. Example drug response curves for HCC1395 treated with cisplatin. Data from three experiments are shown, each plotted in a unique color. Each dot represents the growth inhibition following three days of treatment with one of 10 concentrations of cisplatin. For each dose of each experiment, measurements are performed in triplicate. The x-axis represents increasing cisplatin concentration; the y-axis indicates growth inhibition following treatment. A single curve is fit to the set of 30 data points (3 untreated and 27 treated). The vertical line represents GI50, which is extrapolated from the fitted curve. Across multiple experimental replicates, the dose-response curve is highly reproducible. D, E, F. Example drug response curves for three other cell lines, each treated with a different compound. Convention as in C.

Figure 4:
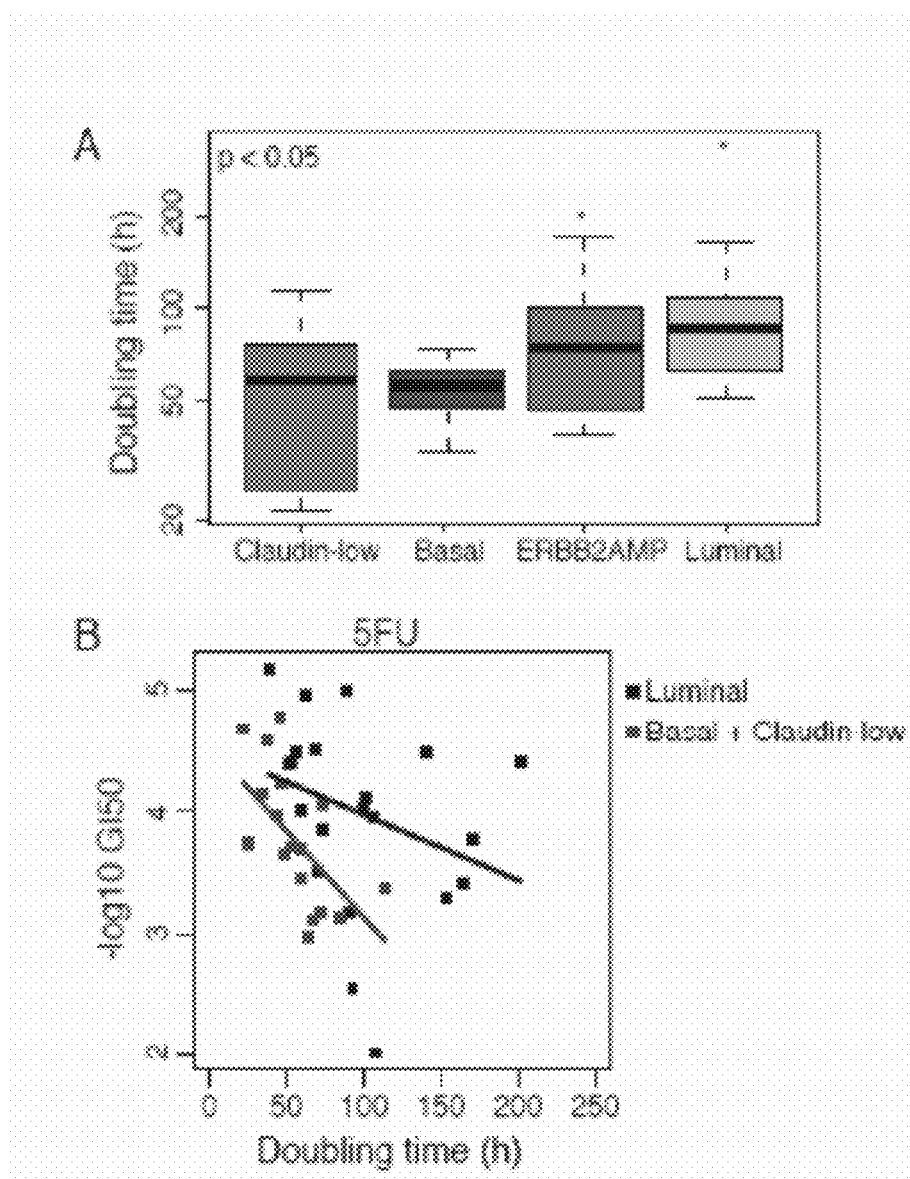

FIG. 4. Doubling time varies across cell line subtype. A. Growth rate, computed as the median doubling time in hours, of the breast cancer cell lines subtypes are shown as boxplots. The basal and claudin-low subtypes have shorter median doubling time as compared to luminal and ERBB2$^{AMP}$ subtypes, Kruskal-Wallis p value (p=0.006). B. The ANCOVA model shows strong effects of both subtype and growth rate on response to 5-FU. Luminal (black) and basal/claudin-low (red) breast cancer lines each show significant associations to growth rate but have distinct slopes.

Figure 5:
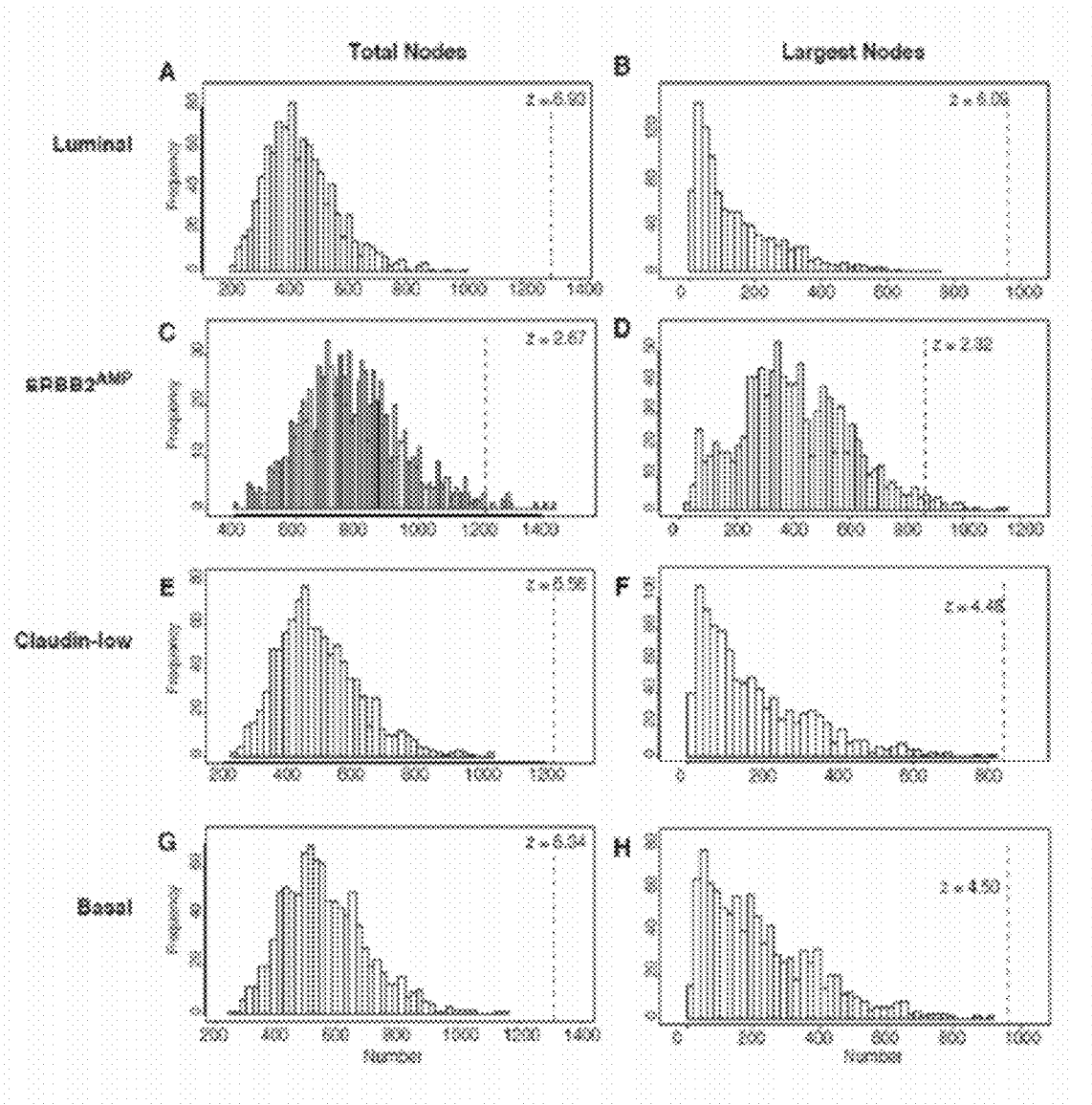
Figure 6A:
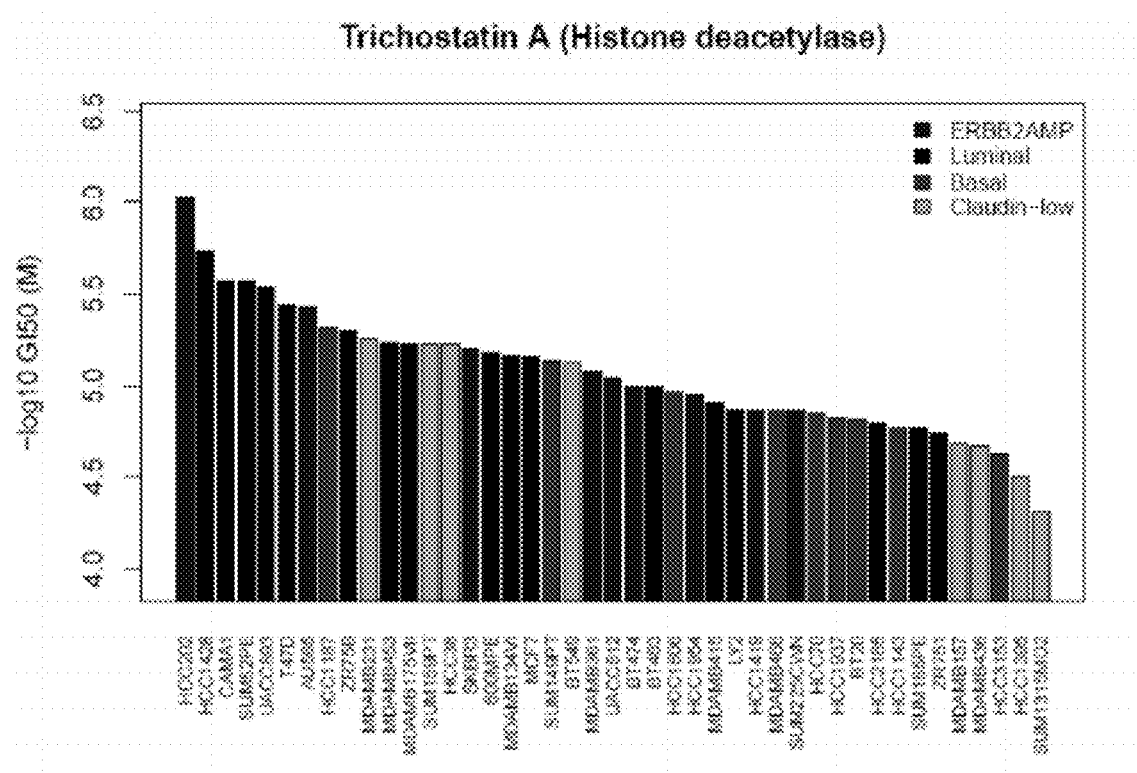
Figure 6D:
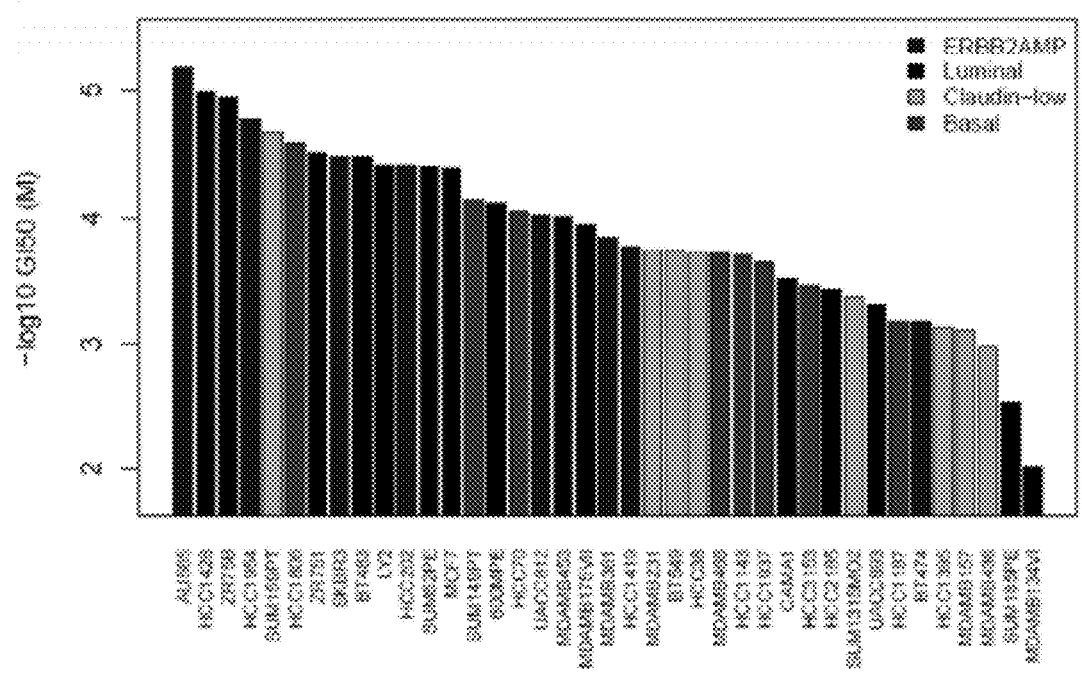
Figure 6E:
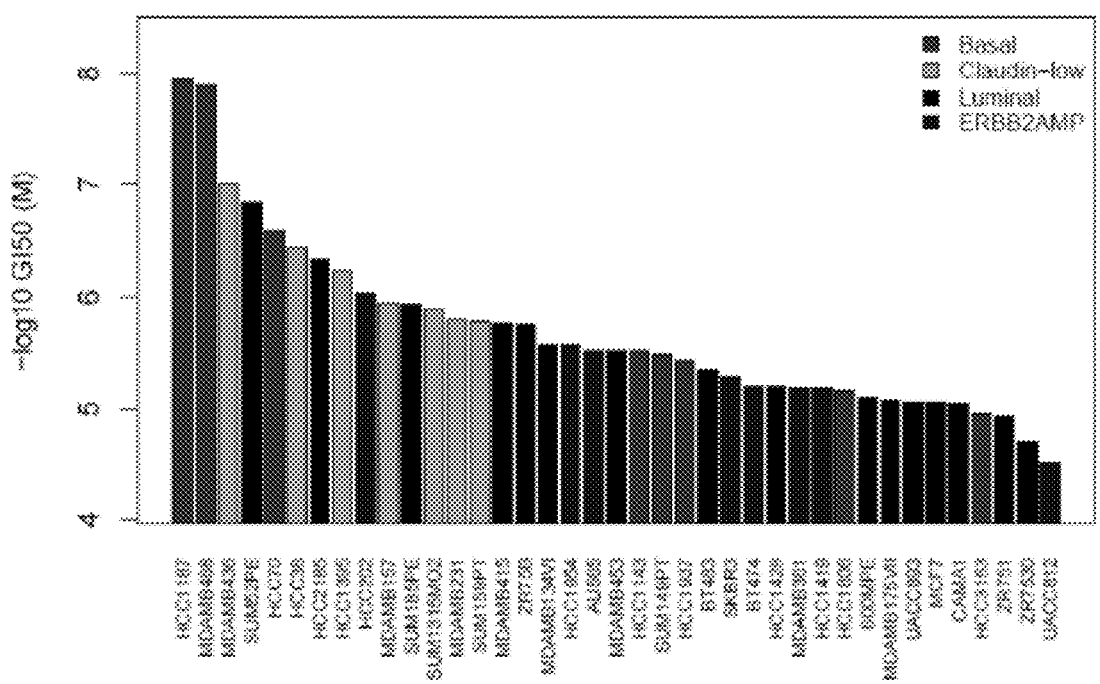
Figure 6F:
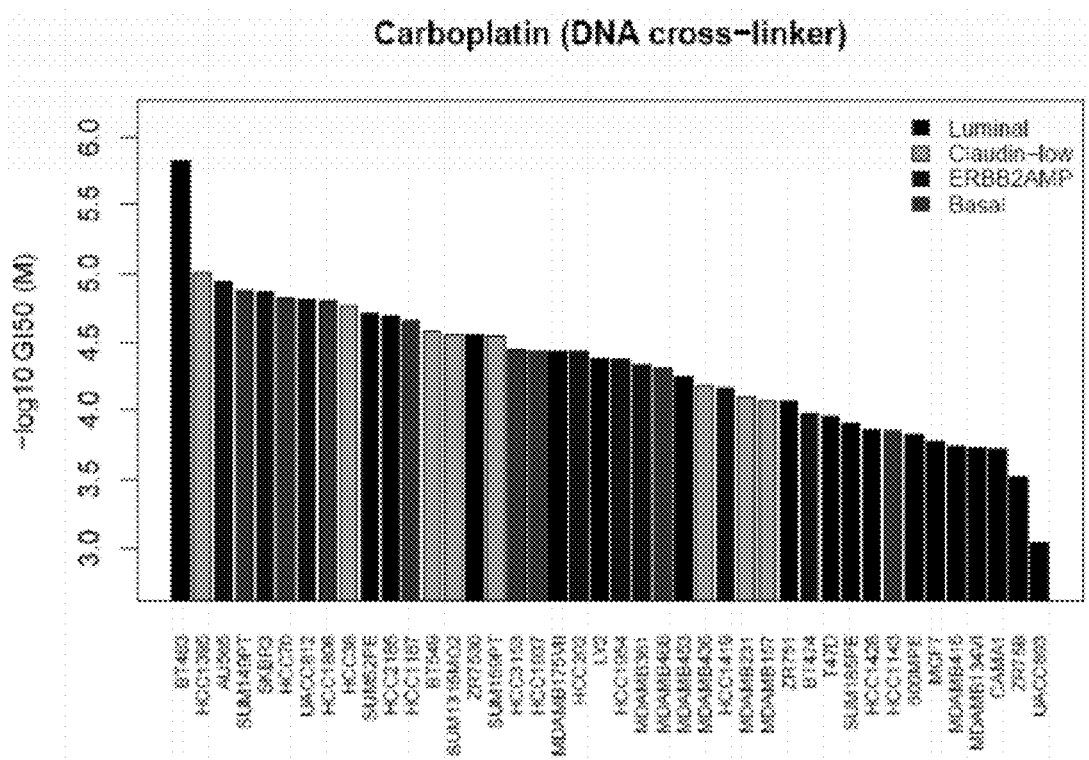
Figure 6J:
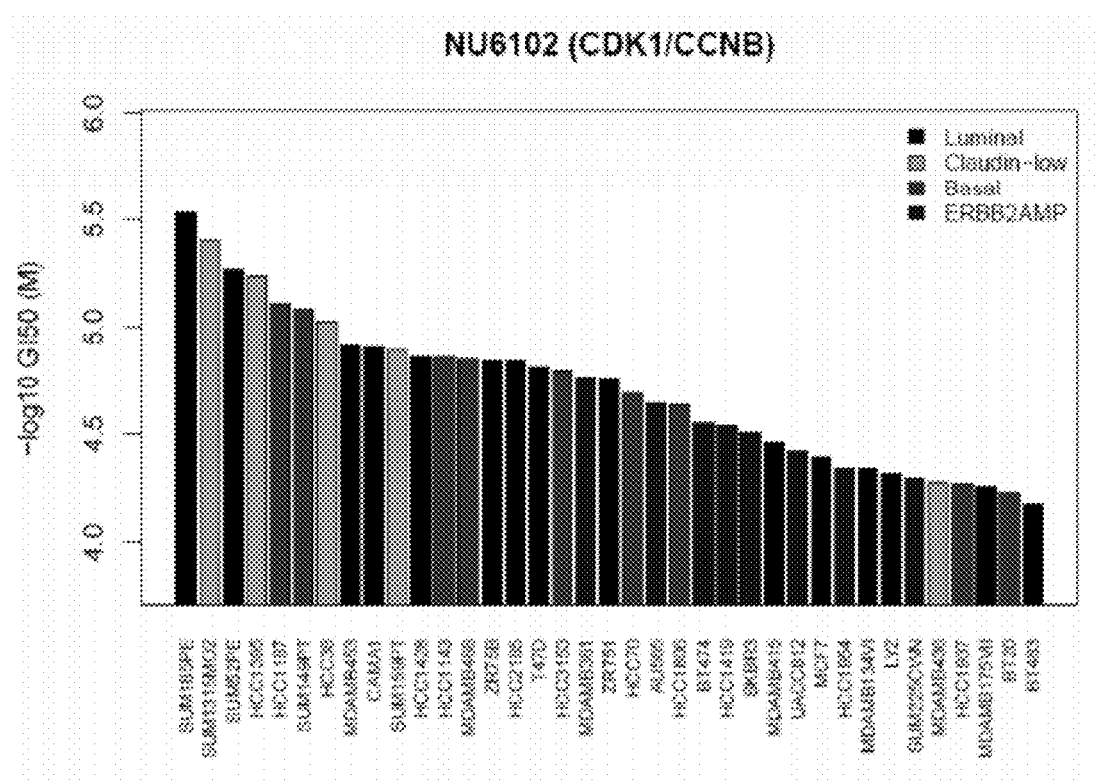

FIG. 5. The cell line networks are highly significant. The significance of the subpathways identified by our method was assessed by comparing the size of our subpathways to the size of the subpathways generated from a background model in which cells were randomly partitioned into groups, rather than in the original subtype definitions. The subpathway sizes were measured in two ways, the total number of nodes in the subpathway (A,C,E,G) and the number of nodes in the largest connected component of the subpathway (B,D,F,H). The luminal (A,B), ERBB2$^{AMP}$ (C,D), claudin-low (E,F), and basal (G,H) subpathway sizes are shown as red dotted lines compared against the distribution of null subpathway sizes. In all cases the subpathway sizes for the true subtype partitioning are significantly larger than the subpathway sizes for the background model.

FIG. 6A-J provides waterfall plots of breast cancer subtypes and anti-cancer compounds. Association of clinical subtypes of breast cancer cell lines with selected anti-cancer compounds are shown. Each bar represents response sensitivity for one cell line, cell lines are ordered by sensitivity ($-\log 10(GI50)$) and colored to indicate subtype.

Table 1. Compounds with significant associations with specific breast cancer subtypes.

Table 2. Transcriptional, genomic and phenotypic characteristics of cell lines in the panel.

Table 3. Drug response data for each cell line tested against 77 therapeutic compounds. Data are $-\log 10$ transformed. These data were used to determine subtype specific responses. A tab delimited .txt file is provided for this table.

Table 4. Pearson correlations between drug responses for all compound pairs. A tab delimited .txt file is provided for this table.

Table 5. Subtype associations for all therapeutic compounds. Both raw p-values and FDR-corrected q-values are shown.

Table 6. Censored drug response data. GI50 values that are same as maximum experimental concentration used for different drugs were removed. Data are $-\log 10$ transformed. These data were used to identify responses associated with copy number aberrations. A tab delimited .txt file is provided for this table.

LENGTHY TABLES

The patent contains a lengthy table section. A copy of the table is available in electronic form from the USPTO web site (http://seqdata.uspto.gov/?pageRequest=docDetail&DocID=US09506926B2). An electronic copy of the table will also be available from the USPTO upon request and payment of the fee set forth in 37 CFR 1.19(b)(3).

DETAILED DESCRIPTION OF THE PREFERRED EMBODIMENT

Preclincial testing in panels of cell lines that mirror molecular subtypes found in primary tumors promises to allow early and efficient identification of responsive molecular subtypes as a guide to early clinical trials. Evidence for the utility of this approach comes from studies showing that cell line panels predict responses in (a) lung cancers with EGFR mutations to gefitinib (Paez J G, et al. (2004) EGFR mutations in lung cancer: correlation with clinical response to gefitinib therapy. *Science* 304(5676):1497-1500), (b) breast cancers with ERBB2 amplification to trastuzumab (Neve R M, et al. (2006) A collection of breast cancer cell lines for the study of functionally distinct cancer subtypes. *Cancer Cell* 10(6):515-527) and/or lapatinib (Konecny G E, et al. (2006) Activity of the dual kinase inhibitor lapatinib (GW572016) against HER-2-overexpressing and trastuzumab-treated breast cancer cells. *Cancer Res* 66(3):1630-1639), and (c) tumors with mutated or amplified BCR-ABL to imatinib mesylate (Scappini B, et al. (2004) Changes associated with the development of resistance to imatinib (STI571) in two leukemia cell lines expressing p210 Bcr/Abl protein. *Cancer* 100(7):1459-1471) The NCI's Discovery Therapeutic Program (DTP) has pursued this approach on large scale identifying associations between molecular features and responses to >100,000 compounds in a collection of ~60 cancer cell lines (Weinstein J N (2006) Spotlight on molecular profiling: "Integromic" analysis of the NCI-60 cancer cell lines. *Mol Cancer Ther* 5(11):2601-2605; Bussey, K. J. et al. Integrating data on DNA copy number with gene expression levels and drug sensitivities in the NCI-60 cell line panel. *Mol Cancer Ther* 5, 853-867 (2006)). Although useful for detecting drugs with diverse responses, the NCI60 panel is arguably of limited power in detecting subtype specific responses because of the relatively sparse representation of specific cancer subtypes in the collection. In breast cancer for example, the collection carries only 6 cell lines. Thus, we have promoted the use of a collection of ~50 breast cancer cell lines for statistically robust identification of associations between response and molecular subtype in breast cancer. Here we report the assessment of associations between quantitative growth inhibition responses and molecular subtypes for 77 compounds including both FDA approved and investigational agents.

From a single set of analyses we generated and report here five of these compounds which are FDA approved agents or compounds and the molecular subtypes of breast cells which respond to at least one of the five compounds. Based on the demonstrated relationship between each clinical agent and a molecularly based classifier that segregates types of breast cancer cell lines—and by extension, types of breast tumors—that respond to the agent from those that do not, herein are described diagnostic or prognostic methods for determining a patient who would respond favorably to each of the five compounds and methods and bases for proposing therapeutic regimens that can be adopted for suitable patients.

The five compounds, Vorinostat, Trichostatin A, Erlotinib, Fluoruracil, GSK1070916, and the molecular subtypes where the five compounds show preferential activity can be categorized as follows:

TABLE 7

| Molecular Subtype | Therapeutic Compound with Preferential Activity |
| --- | --- |
| Luminal (ER+/PR+) | Vorinostat, Trichostatin A |
| Basal (ER-/PR-/HER2-Claudin+) | Erlotinib, Fluoruracil |
| Claudin-low | GSK1070916, Fluoruracil |
| KI67+ tumors | Fluoruracil |
| Tumors with low or no 20q13 amplification | GSK1070916 |

In summary, the following was found that:

Vorinostat is preferentially active in luminal class cell lines. This corresponds to ER+/PR+ tumors in clinical studies.

Trichostatin A is preferentially active in luminal class cell lines. Again, this corresponds to ER+/PR+ tumors in clinical studies.

Erlotinib is preferentially active in basal class cell lines. This corresponds to the ER-/PR-/HER2-Claudin+ tumor subtype conventionally described as triple negative.

The compound identified as GSK.AUR1 (also known as GSK1070916) by GlaxoSmithKline, is preferentially active against Claudin-low cell lines, which corresponds to the recently identified, but rare Claudin-low tumor subtype.

Fluorouracil (5FU) is active against cell lines with rapid growth rates. This does not have a molecular correlate at the present time but might correspond to measure of KI67 staining which measures growth rate in tumors. Fluoruracil once factoring out growth rate, is more effective against basal cell lines (both triple negative and claudin-low) than against luminal cell lines. This corresponds to the conventional triple negative subset of breast cancers.

GSK.AUR1 (GSK1070916) is less effective in tumors that have genomic DNA copy number amplifications at 20q13, which includes the AURKA locus which is notably one of the targets of the GSK.AUR1 inhibitor.

In some embodiments of the invention, a method for identifying a cancer patient suitable for treatment with an anti-cancer agent selected from the group of vorinostat, trichostatin A, Erlotinib, fluoruracil, and GSK1070916, comprising: (a) measuring the expression level of a target gene in a sample from the patient; and (b) comparing the expression level of said gene from the patient with the expression level of the gene in a normal tissue sample or a reference expression level (such as the average expression level of the gene in a cell line panel or a cancer cell or tumor panel, or the like), wherein an increase or decrease in the expression level of the target gene indicates the patient is suitable for treatment with one of the selected anti-cancer agents.

In one embodiment, the method, further comprising (c) measuring the genomic copy number or expression level of a gene encoding ER and PR in a sample from the patient, and (d) comparing the ER and PR genomic copy numbers in the patient to normal copy number or expression level of the genes encoding ER and PR, the expression level of the genes encoding ER and PR in a normal tissue sample or a reference expression level, or the average expression level of ER and PR in a panel of normal cell lines or cancer cell lines, wherein a positive level or an increase in the expression level of ER and PR indicates the patient is suitable for treatment with vorinostat or trichostatin A. In another embodiment, the method, further comprising (c) measuring the HER2 protein levels in a sample from the patient, and (d) comparing the ER and PR protein levels from the sample to normal ER and PR protein levels in a normal tissue sample or a reference protein level, or the average protein level of ER and PR in a panel of normal cell lines or cancer cell lines, wherein positive level or an increase in the protein levels of ER and PR indicates the patient is suitable for treatment with vorinostat or trichostatin A. Patients identified by the present invention may also respond to synergistic treatment of cancer with both vorinostat or trichostatin A.

In one embodiment, the invention provides for a method of treating a cancer patient comprising (a) identifying a cancer patient who is suitable for treatment with one of five identified clinical agents, Vorinostat, Trichostatin A, Erlotinib, Fluoruracil, or GSK1070916, and (b) administering a therapeutically effective amount of the clinical agent. In some embodiments, a combination of the selected clinical agent and another known anti-cancer agent, and in other embodiments, the selected clinical agent and another known anti-cancer agent are administered concurrently or sequentially.

In another embodiment, the invention provides for a method of treating a cancer patient comprising (a) obtaining a biopsy of a cancer patient and identifying the cellular subtype of the cells in said cancer patient; (b) determining if the subtype is suitable for treatment with one of five identified clinical agents, Vorinostat, Trichostatin A, Erlotinib, Fluoruracil, or GSK1070916, and (b) administering a therapeutically effective amount of the clinical agent.

The present methods describe the measurement and detection of the expression level of a gene as measured from a sample from a patient that comprises essentially a cancer cell or cancer tissue of a cancer tumor. Such methods for obtaining such samples are well known to those skilled in the art. When the cancer is breast cancer, the expression level of a gene is measured from a sample from the patient that comprises essentially a breast cancer cell or breast cancer tissue of a breast cancer tumor.

Methods for detection of expression levels of a gene can be carried out using known methods in the art including but not limited to, fluorescent in situ hybridization (FISH), immunohistochemical analysis, comparative genomic hybridization, PCR methods including real-time and quantitative PCR, and other sequencing and analysis methods. The expression level of the gene in question can be measured by measuring the amount or number of molecules of mRNA or transcript in a cell. The measuring can comprise directly measuring the mRNA or transcript obtained from a cell, or measuring the cDNA obtained from an mRNA preparation thereof. Such methods of extracting the mRNA or transcript from a cell, or preparing the cDNA thereof are well known to those skilled in the art. In other embodiments, the expression level of a gene can be measured by measuring or detecting the amount of protein or polypeptide expressed, such as measuring the amount of antibody that specifically binds to the protein in a dot blot or Western blot. The proteins described in the present invention can be overexpressed and purified or isolated to homogeneity and antibodies raised that specifically bind to each protein. Such methods are well known to those skilled in the art.

Comparison of the detected expression level of a gene in a patient sample is often compared to the expression levels detected in a normal tissue sample or a reference expression level. In some embodiments, the reference expression level can be the average or normalized expression level of the gene in a panel of normal cell lines or cancer cell lines.

Methods of assaying for ERBB2 or HER2 protein overexpression include methods that utilize immunohistochemistry (IHC) and methods that utilize fluorescence in situ hybridization (FISH). A commercially available IHC test is DAKO HercepTest® (DAKO Corp., Carpinteria, Calif.). Patient samples having an IHC staining score of 0-1,2 is normal, and scores of 2+ may be borerderline, while results of 2,3+ are scored as positive for multiple copies of HER2 (HER2 positive).

A commercially available FISH test is PathVysion® (Vysis Inc., Downers Grove, Ill.). The HER2 genomic copy number of a patient sample is determined using FISH. Generally if a sample is found to have 3.6 or more copies of HER2 (normal=2 copies), the patient is determined to be HER2 positive.

While many HER2-positive patients suffer from metastatic breast cancer, a patient's HER2 and other tumor cell subtype status can also be determined in relation to other types of cancers including but not limited to epithelial cancers such as pancreatic, lung, cervical, ovarian, prostate, non-small cell lung carcinomas, melanomas, squamous cell cancers, etc. It is contemplated that the present methods described herein may find use in prognosis and predicting patient response to the five compounds that may be used in various cancer treatments for multiple types of cancers so long as the patient criteria described herein is present as identifying a patient suitable for the targeted therapy.

EXAMPLES

Example 1

Identification of Molecular Predictors of Response to 74 Compounds

The utility of cell lines for identification of clinically useful molecular predictors of response depends on the extent to which the diverse molecular mechanisms that determine drug response are operative in the cell line panel. We have reported previously on similarities and differences between the cell lines and primary tumors at the transcription and genome copy number level and we refine that comparison here using higher resolution platforms.

The potential clinical utility of these findings is supported by the fact that in vitro derived molecular predictors of response to therapeutic compounds are concordant with clinical results. For example, ERBB2-amplified cell lines are preferentially sensitive to ERBB2-targeted agents and basal subtype cell lines are preferentially sensitive to platinum salts, as observed clinically. That said, additional work remains before the signatures reported in this study can be used to select patients for clinical trials. This includes development of robust and reliable molecular assays that can be applied to clinical samples, establishment of predictive algorithms with decision making thresholds optimized for clinical use, and validation of predictive power in multiple independent studies. To initiate this process, we suggest that the response associated signatures identified in this study be developed into standardized assays that can be assessed for clinical predictive power in early stage clinical trials and used to design trials that are properly powered to detect the responses in the clinical subsets predicted by the in vitro studies. Assays that show positive predictive power in early clinical trials can then be "locked down" and tested for predictive power in follow-on clinical trials.

We anticipate that the power of this in vitro systems approach will increase as additional molecular features including mutations, methylation and alternative splicing, are included in the analysis. In addition, expanding the cell line panel will increase the power to identify low frequency molecular patterns, and to develop robust predictive models. Most important, however, is iterative refinement of the in vitro assay system based on lessons learned by comparing in vitro predictions with clinical reality Cell Line Characteristics.

Specifically, we used hierarchical consensus clustering (HCC) of gene expression profiles to classify 50 breast cancer cell lines and 5 non-malignant breast cell lines into three transcriptional subtypes: luminal, basal and the newly described claudin-low (Table 2; PMID 19435916). These subtypes are related to those described earlier[1] (FIG. 2) but improved methodology and increased data have refined these classes. We added a fourth class (ERBB2$^{AMP}$) comprised of cell lines with DNA amplification of ERBB2 to reflect the clinically distinct treatment category of Her2 positive tumors with the ERBB2-targeted inhibitors lapatinib and trastuzumab. Finally, a refined high resolution SNP copy number analysis (FIG. 2B confirms that the cell line panel models regions of recurrent amplification at 11q13 (CCND1), 17q12 (ERBB2), 20q13 (STK15), or homozygous deletion at 9p21 (CDKN2A)) found in primary tumors. Altogether, this concordance between cell lines and breast tumors suggests that cell line subtype mirror the much of the breast tumor diversity found in patients.

Drug Effects on Cell Lines.

To examine heterogeneity in drug response across the cell line panel, we assessed quantitative responses to 77 compounds that are anti-cancer agents across the cell line panel using a cell growth assay with a quantitative endpoint measured at three days of continuous exposure to each agent (Table 3). The anti-cancer agents included clinically approved agents and compounds still in the product development cycle with a mix of conventional cytotoxic agents (e.g. taxanes, platinols, anthracylines) and targeted agents (e.g. SERMs, and kinase inhibitors). In many cases, several agents targeting the same protein or molecular mechanism of action were tested. A variety of response measures were assessed including the concentration of drug required to inhibit growth by 50% ($GI_{50}$), the concentration necessary to completely inhibit growth (Total Growth Inhibition, TGI) and the concentration of drug necessary to reduce the population to 50% of the initial number (Lethal Concentration 50%, $LC_{50}$).

The design of the assay and the sensitivities of the cell lines necessitated that even at the highest drug concentrations tested, for some cell lines one or more of the three responses was not reached for any given drug. In cases where the underlying growth data are of high quality, but the end point response (GI50, TGI, LC50) was not reached the values were set to the highest concentration tested. $GI_{50}$ values represent the lowest threshold for accurate and diverse data and are the basis for the remainder of our analysis. $GI_{50}$ values were obtained for each cell line and compound pair that was successfully measured. We excluded three compounds (PS1145, cetuximab and baicalein) from further analysis because almost none of the cell lines in the panel responded strongly.

Figure 1B:
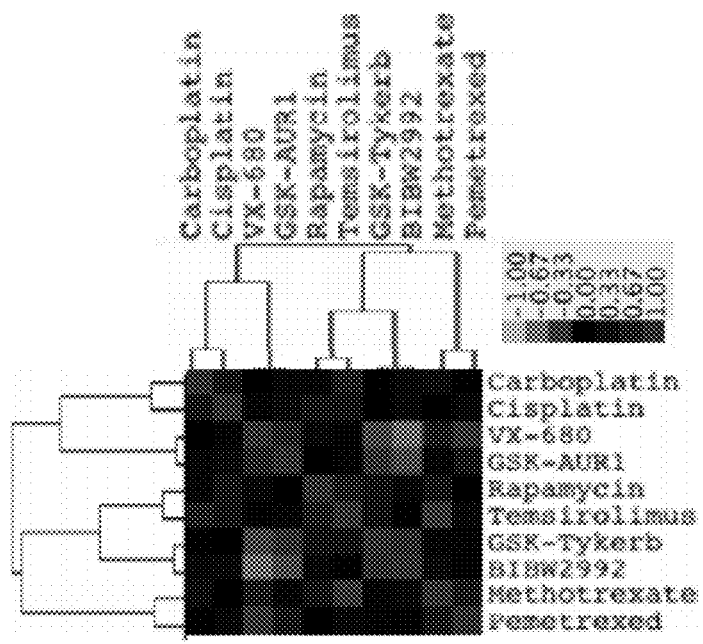

A representative waterfall plot showing the variation in response to the Sigma AKT1-2 inhibitor is shown in FIG. 1A. We established the reproducibility of the overall data set by making replicate determinations and median absolute deviation (MAD) of $GI_{50}$ values for 272 drug/cell line combinations with at least 3 replicates. We found that the median MAD was remarkably constant, just 0.16, regardless of number of replicates (FIG. 2). Response profiles among the cell lines were generally similar for compounds targeting similar mechanisms of action (FIG. 1B and Table 4).

In Vitro $GI_{50}$ to and Clinical Relevance.

A central goal of this study was to use the mappings between the breast cancer cell lines and actual tumors to establish predictors of clinical response for each. We started our analysis by examining associations with the four cell line subtypes defined above (luminal, basal, claudin-low and ERBB2$^{AMP}$). The Kruskal-Wallis test, a non-parametric test, was used to establish associations of these subtypes with responses to the 74 therapeutic agents. Overall, 23 of 74 compounds tested and nearly all of the agents producing strong differential responses across the cell line panel produced subtype specific responses (p<0.1 after FDR correction of 222 p-values from all three groups). FIG. 1C shows a hierarchical clustering of the 26 agents with significant associations to one or more of the subtypes tested (see also Table 1 and Table 5).

The top ten most subtype-associated agents were inhibitors of aspects of receptor tyrosine kinase signaling and histone deacetylase (Table 1), which had highest efficacy in luminal and ERBB2$^{AMP}$ cell lines. Docetaxel, etoposide, and cisplatin showed preferential activity in basal or claudin-low cell lines, providing in vitro support for the hypothesis that the standard chemotherapeutic agents are of benefit to patients with triple negative or basal-like tumors (PMID 17438091, 20100965). Agents targeting the mitotic apparatus, including GSK1070916 (AURK B/C inhibitor), also were more active against basal and/or claudin-low cell lines.

Figure 1D:
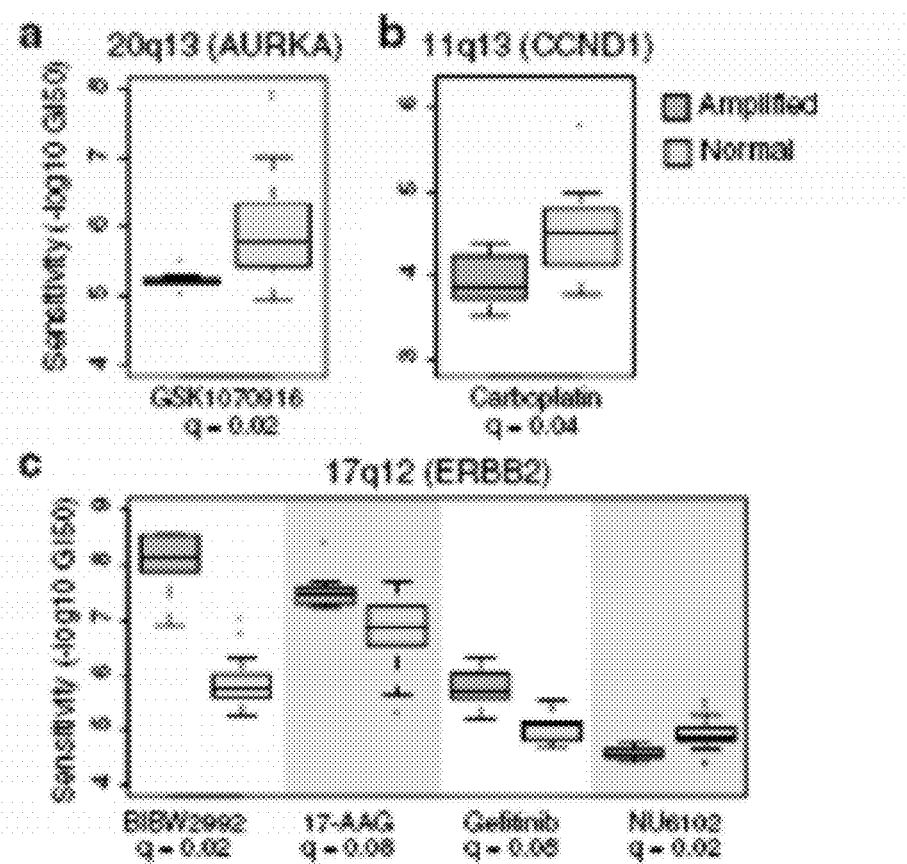

Our next effort was focused on using the readily testable nature of focal high-level copy number aberrations in the clinical setting, allowing stratification of the patient populations (and breast cancer cell lines) based on their occurrence. The four regions of recurrent copy number aberration defined above produced 6 significant associations to single agents (FIG. 1D). Amplification at 20q13, encoding AURKA, was associated with resistance to the AURK B/C inhibitor GSK1070916 (Hardwicke M A, et al. (2009) GSK1070916, a potent Aurora B/C kinase inhibitor with broad antitumor activity in tissue culture cells and human tumor xenograft models. *Mol Cancer Ther* 8(7):1808-1817). This suggests that amplification of AURKA provides a bypass mechanism for AURK B/C inhibitors. Amplification at 11q13, encoding CCND1, was associated with resistance to carboplatin. CCND1 is a G1/S cell cycle checkpoint gene that monitors for unrepaired DNA damage, and whose over-expression is known to be associated with cisplatin resistance in other tumor types (Nakashima T, et al. (2005) The effect of cyclin D1 overexpression in human head and neck cancer cells. *Eur Arch Otorhinolaryngol* 262(5):379-383, Huerta S, et al. (2003) Gene expression profile of metastatic colon cancer cells resistant to cisplatin-induced apoptosis. *Int J Oncol* 22(3):663-670). Amplification at 17q12 (ERBB2) was associated with sensitivity to BIBW2992 and gefitinib, inhibitors of ERBB2 and/or EGFR, as well as 17-AAG (HSP90AA1). 17q12 amplification was also associated with resistance to the CDK1/CCNB1 inhibitor, NU6102, which may reflect the fact that ERBB2 negatively regulates CDK1 (Yu D, et al. (1998) Overexpression of ErbB2 blocks Taxol-induced apoptosis by upregulation of p21Cip1, which inhibits p34Cdc2 kinase. *Mol Cell* 2(5):581-591, Tan M, et al. (2002) Phosphorylation on tyrosine-15 of p34(Cdc2) by ErbB2 inhibits p34(Cdc2) activation and is involved in resistance to taxol-induced apoptosis. *Mol Cell* 9(5):993-1004), thereby diminishing the impact of the CDK1 inhibitor.

Agent Response and Other Cell Line Properties.

In general, luminal subtype cell lines grow more slowly than basal or claudin-low cells (Kruskal-Wallis p=0.006, FIG. 4A) and the range of doubling times is broad. This raises the possibility that the cell lines that are most sensitive to the compounds tested are those that grow most rapidly. If so, then the observed associations to subtype could represent an association to an obvious covariate. We tested this hypothesis by assessing the effects of subtype and doubling time simultaneously using ANCOVA and observed that 20 of 23 compounds had better associations with subtype than with doubling time (mean log ratio of p-values=0.87, standard deviation 1.09). This identifies subtype membership (or an unmeasured covariate), rather than doubling time as the major driver of drug response. Moreover, 11 of 23 subtype specific compounds were more effective in the more slowly growing luminal cell lines (Table 1), which would be inconsistent with the hypothesis that only fast growing cells are easily inhibited. One agent, 5-florouracil, is not significant in the subtype test alone but shows strong significance in the ANCOVA model for both class and doubling time. The response to 5-florouracil decreases as doubling time increases in both luminal and basal cell lines show this pattern but the mean sensitivity shifts by approximately one log between the subtypes (FIG. 4B).

1) Vorinostat is preferentially active in luminal class cell lines. This corresponds to ER+/PR+ tumors in clinical studies.

2) Trichostatin A is preferentially active in luminal class cell lines. Again, this corresponds to ER+/PR+ tumors in clinical studies.

3) Erlotinib is preferentially active in basal class cell lines. This corresponds to the ER-/PR-/HER2-Claudin+ tumor subtype conventionally described as triple negative.

4) The compound identified as GSK.AUR1 (also known as GSK1070916) provided to our group by GlaxoSmithKline, is preferentially active against Claudin-low cell lines, which corresponds to the recently identified, but rare Claudin-low tumor subtype.

5) Fluorouracil (5FU) is active against cell lines that grow more quickly than tumors than grow more slowly. This does not have a molecular correlate at the present time but might correspond to measure of KI67 staining which measures growth rate in tumors.

6) Fluoruracil once factoring out growth rate, is more effective against basal cell lines (both triple negative and claudin-low) than against luminal cell lines. This corresponds to the conventional triple negative subset of breast cancers.

7) GSK.AUR1 is less effective in tumors that have genomic DNA copy number amplifications at 20q13, which includes the AURKA locus one of the targets of the GSK.AUR1 inhibitor.

Cell Culture and Nucleotide Isolation.

Fifty-six breast cancer cell lines were cultured and nucleotides were isolated as described previously in Neve R M, et al. (2006) A collection of breast cancer cell lines for the study of functionally distinct cancer subtypes. *Cancer Cell* 10(6):515-527.

Cell Growth Inhibition Assay.

Cells were plated at a density in 96-well plates such that they would remain in log growth at the end of assay time. The cells were allowed to attach overnight before being exposed to drug for 72 h. Compounds were dissolved in a stock solution of either dimethyl sulfoxide (DMSO) or water, and a set of 9 doses in 1:5 serial dilution was added in triplicate wells. The final DMSO concentration in the treated well was 0.3% or less. The cell growth was determined using Cell Titer Glo assay (CellTiter-Glo Luminescent Cell Viability Assay, Promega, Madison, Wis., USA), with slight modification from the manufacturer's protocol at day 0 (time when drug was added) and day 3 of drug exposure. Briefly, Cell Titer Glo reagent was diluted with phosphate-buffered saline (1:1 v:v) and the culture media was removed from the 96-well plate prior to adding 50 µl per well of the diluted Cell Titer Glo reagent. Luminescence from the assay was recorded using BIO-TEK FLx800. From the untreated control wells, CTG luminescence were measured at day 0 and day 3 (72 hr later).

Measurement of Growth Rate in Cell Lines.

Doubling time (DT) was estimated from the ratio of 72 h to 0 h for untreated wells.

Analysis of Drug Response Data.

Each set of drug response data consists of measures of the relative amounts of cells still viable after a sample is subjected to nine 5-fold serial dilutions of a given drug with 3 replicates each, for a total of 27 observations. A plot of these observations with relative viability on the y-axis and the log of drug concentrations increasing on the x-axis suggest a monotonically decreasing curve bounded above and below on the y-axis. We used a custom-written R package to fit a curve to the drug response data and calculate a measure of drug sensitivity.

Specifically, we used nonlinear least squares to fit these observations, along with three replicates of the vehicle control values, with a four-parameter Gompertz curve. Two of the parameters represent the upper and lower asymptotes of the curve, and the other two adjust the slope and point of inflection. We used a Gompertz model because it allows for flexibility and asymmetry about the inflection point. The fitted curve for each set is then transformed into a GI curve, using the method described by the NCI/NIH DTP Human Tumor Cell Line Screen Process (Russ, A. P. & Lampel, S., The druggable genome: an update. *Drug Discov Today* 10 (23-24), 1607-1610 (2005)) and as previously described in Monks, A. et al., Feasibility of a high-flux anticancer drug screen using a diverse panel of cultured human tumor cell lines. *J Natl Cancer Inst* 83 (11), 757-766 (1991). The percent growth curve is calculated as $[(T-T0)/(C-T0)] \times 100$, where T0 is the cell count at day 0, C is the vehicle control (for example 0.3% DMSO without drug) cell count at day 3, and T is the cell count at the test concentration. The GI50 value is determined as the drug concentration that results in 50% growth at 72 h drug exposure.

We filtered the drug response data on four quality control metrics: 1) median standard deviation across the 9 concentrations less than 0.20; 2) doubling time within 2 standard deviations of the median doubling time for a particular cell line; 3) slope of the fitted Gompertz curve to be greater than 0.25; 4) growth inhibition at the maximum concentration less than 50% for cell line/drug combinations with no clear response. Approximately 80% of the drug plates pass all filtering requirements.

SNP Array Processing and DNA Copy Number Analysis.

Affymetrix Genome-Wide Human SNP Array 6.0 quality and data processing was performed using the R statistical framework (R-project website) based aroma.affymetrix6. The breast cancer cell line SNP arrays were normalized using 20 normal sample arrays as described in Bengtsson, H., Irizarry, R., Carvalho, B., & Speed, T. P., Estimation and assessment of raw copy numbers at the single locus level. *Bioinformatics* (Oxford, England) 24 (6), 759-767 (2008). The raw copy number for each sample obtained from aroma.affymetrix were segmented using circular binary segmentation (CBS) algorithm using R and Bioconductor (Gentleman, R. C. et al., Bioconductor: open software development for computational biology and bioinformatics. *Genome biology* 5 (10), R80 (2004)) based DNAcopy (Olshen, A. B., Venkatraman, E. S., Lucito, R., & Wigler, M., Circular binary segmentation for the analysis of array-based DNA copy number data. *Biostatistics* (Oxford, England) 5 (4), 557-572 (2004)). The significant DNA copy number changes were analyzed using MATLAB based Genomic Identification of Significant Targets in Cancer (GISTIC) as described in Beroukhim, R. et al., Assessing the significance of chromosomal aberrations in cancer: methodology and application to glioma. *Proceedings of the National Academy of Sciences of the United States of America* 104 (50), 20007-20012 (2007).

Drug Screening.

Each drug included in the statistical analysis satisfied the following screening criteria for data quality:

Missing values—No more than 40% of GI50 values can be missing across the entire set of cell lines.

Variability—For at least 3 cell lines, either $$GI50 > 1.5 \cdot GI50_{median}, \text{ or}$$

$$GI50 < 0.5 \cdot GI50_{median}$$

where $GI50_{median}$ is the median GI50 for a given drug. Any compounds failing these criteria were excluded from the statistical analysis. Source code for the screening algorithm is included with Supplementary Information.

Exon Array Processing.

Gene expression data for the cell lines were derived from Affymetrix GeneChip Human Gene 1.0 ST exon arrays. Gene-level summaries of expression were computed using the aroma.affymetrix R package (Bengtsson et al, 2008), with quantile normalization and a log-additive probe-level model (PLM) based on the HuEx-1_0-st-v2, DCCg, Spring 2008 CDF. Transcriptional profiles derived from the Affymetrix exon arrays have been shown to accord well with those derived from Affymetrix HG-U133 Plus 2.0 arrays (Pradervand et al, 2008). Transcript identifiers were converted to HGNC gene symbols by querying the Ensembl database using the BioMart R package. The resulting expression profiles were subsequently filtered to capture only those genes expressing a standard deviation greater than 1.0 on the $log_2$-scale across all cell lines.

Consensus Clustering.

Cell line subtypes were identified using hierarchical consensus clustering (Monti et al, 2003). Consensus was computed using 500 samplings of the cell lines, 80% of the cell lines per sample, agglomerative hierarchical clustering and average linkage. R source code is included with Supplementary Information.

Merging of Microarray Datasets.

A gene expression microarray dataset (GSE10885) containing breast tumors with all the five breast cancer subtypes and metaplastic breast tumors2 were obtained from Gene Expression Omnibus (GEO) 10. Breast cancer cell line and breast tumor gene expression profiles were screened by selecting gene symbols with standard deviation (SD)>0.8. The merging of SD selected datasets was performed using DWD as described 11,12. Each dataset was column (samples) normalized to N(0,1) and row (genes) normalized by median centering. The processed datasets were merged using Java base DWD (Benito, M. et al., Adjustment of systematic microarray data biases. *Bioinformatics* (Oxford, England) 20 (1), 105-114 (2004)) and finally, median centered across row (genes). HC of the merged dataset was performed using Cluster.

Associations of Subtype and Response to Therapeutic Agents.

Associations between drug response and subtype were assessed for: (a) luminal vs. basal vs. claudin-low; (b) luminal vs. basal+claudin-low; and (c) ERBB2-AMP vs. non-ERBB2-AMP. Differences between $-\log 10(GI_{50})$ of the groups were compared with a non-parametric Kruskall-Wallis ANOVA. The p-values for the three sets of tests were combined and the Benjamini-Hochberg False Discovery Rate (FDR q-value) was used to correct for multiple testing. For the three-sample test, the most sensitive group was identified by performing a post-hoc analysis on the significant compounds in which we compared each group to all others. The p-values for the post-hoc test were adjusted together. In all cases, q<0.10 was deemed significant. If the basal+claudin-low group was significant in scheme 2, but only one of these groups was significant in scheme 1, precedence was given to the 3 sample case when assigning class specificity. There was no minimum difference in medians required.

Association of Growth Rate and Response to Therapeutic Agents.

We performed a 2-way ANCOVA to assess the effects of cell line class and growth rate on drug sensitivity. Specifically, we fit a linear model that looks for a separate regression line for each class of cell lines:

$$GI50 = class + growth\ rate + error$$

We performed a separate ANCOVA for each of the three cell line classification schemes, which yielded 6 sets of p-values (2 main effects×3 classification schemes). We used a single FDR correction to assess significance, and declared FDR p-values<0.20 to be of interest. We performed these analyses in R with the functions lm and Anova, which is available as part of the car package.

Assessment of GI50 Replicates.

We used the median absolute deviation (MAD) to assess the reliability of our replicate measures of GI50. The MAD is a measure of deviation, similar to, but more robust than the standard deviation. We computed the MAD as a function of number of replicates for each drug/cell line combination with more than 3 replicates.

Association of Genomic Changes and Response to Therapeutic Agents.

A t-test was used to assess the association between recurrent copy number changes at 9p21, 11q13, 17q12 and 20q13, as identified in the GISTIC analysis, and drug response. Cell lines with low or no amplification were combined into a single group and compared to cell lines with high amplification. A similar analysis was performed for regions of deletion. Cell lines for which the $GI_{50}$ was equal to the maximum concentration tested were omitted from analysis (e.g., after censoring lapatinib, there were only 2 samples in the amplified copy number group for 17q12; Table S6). Compounds were omitted if the distribution deviated greatly from normality, as assessed by QQ plot. The complete set of p-values was adjusted for multiple comparisons, and q≤0.10 was deemed significant.

Identification of Subtype Pathway Markers

Interconnected genes that collectively showed differential IPLs with respect to subtype were identified by treating each subtype as a dichotomization of the cell lines into a group containing the subtype of interest and a group containing the remaining cell lines.

The R implementation of the two-class Significance Analysis of Microarrays (SAM) algorithm (Tusher V G, Tibshirani R, & Chu G (2001) Significance analysis of microarrays applied to the ionizing radiation response. *Proc Natl Acad Sci USA* 98(9):5116-5121) was used to compute a differential activity (DA) score for each concept in the SuperPathway. For subtypes, positive DA corresponds to higher activity in the subtype compared to the other cell lines.

Integration of Copy Number and Transcription Measurements Identifies Biologically Relevant SuperPathways.

We used the network analysis tool PARADIGM (Vaske C J, et al. (Inference of patient-specific pathway activities from multi-dimensional cancer genomics data using PARADIGM. *Bioinformatics* 26(12):i237-245) to identify pathway based mechanisms that underlie subtype specific responses. PARADIGM uses copy number and transcription data to calculate integrated pathway levels (IPLs) for 1441 curated signal transduction, transcriptional and metabolic pathways (see Kristensen, et al, this issue). We compared IPLs for cell lines and primary breast tumors using data from The Cancer Genome Atlas (TCGA) project (Website for cancergenome.nih.gov), and found a general concordance between transcriptional subtype and pathway activity across the two cohorts (data not shown). This subtype specific pathway activity likely explains much of the observed subtype specific responses.

SuperPathway analysis of differential drug response among the cell lines also revealed subnet activities that provide information about mechanisms of response. For example, basal cell line sensitivity to the DNA damaging agent, cisplatin, was associated with upregulation of a DNA-damage response subnetwork that includes ATM and CHEK1, key genes associated with response to cisplatin (Siddik Z H (2003) Cisplatin: mode of cytotoxic action and molecular basis of resistance. *Oncogene* 22(47):7265-7279) (data not shown). Likewise, ERBB2$^{AMP}$ cell line sensitivity to geldanamycin (HSP90 inhibitor) was associated with upregulation of an ERBB2-HSP90 subnetwork (data not shown). This is consistent with the known ERBB2 degradation induced by geldanamycin binding (Blagosklonny M V (2002) Hsp-90-associated oncoproteins: multiple targets of geldanamycin and its analogs. *Leukemia* 16(4):455-462; Baselga J & Swain S M (2009) Novel anticancer targets: revisiting ERBB2 and discovering ERBB3. *Nat Rev Cancer* 9(7):463-475).

Example 2

Identifying Patient Response to One of Five Compounds Identified

Vorinostat, trichostatin A, Erlotinib, and fluoruracil are currently approved for use in patients with various cancers. For example, patients eligible for erlotinib or fluorouracil therapy would be triple negative (ER-/PR-/HER2-Claudin+) patients. Paraffin embedded tumor blocks from patient biopsy could be assessed for KI67+ staining using standard molecular approaches. If positive for KI67 staining, then the patient should be prescribed fluorouracil.

On the other hand, patients with cancers found to be ER+/PR+ would be instead prescribed vorinostat or trichostatin A. Thus, determining the patient response profile will eliminate therapies to patients where response is predicted to be resistant.

REFERENCES

1 Neve, R. M. et al., A collection of breast cancer cell lines for the study of functionally distinct cancer subtypes. *Cancer cell* 10 (6), 515-527 (2006).

2 Hennessy, B. T. et al., Characterization of a naturally occurring breast cancer subset enriched in epithelial-to-mesenchymal transition and stem cell characteristics. *Cancer research* 69 (10), 4116-4124 (2009).

3 Serrano, M., Hannon, G. J., & Beach, D., A new regulatory motif in cell-cycle control causing specific inhibition of cyclin D/CDK4. *Nature* 366 (6456), 704-707 (1993).

4 Russ, A. P. & Lampel, S., The druggable genome: an update. *Drug Discov Today* 10 (23-24), 1607-1610 (2005).

5 Monks, A. et al., Feasibility of a high-flux anticancer drug screen using a diverse panel of cultured human tumor cell lines. *J Natl Cancer Inst* 83 (11), 757-766 (1991).

6 Bengtsson, H., Irizarry, R., Carvalho, B., & Speed, T. P., Estimation and assessment of raw copy numbers at the single locus level. *Bioinformatics* (Oxford, England) 24 (6), 759-767 (2008).

7 Gentleman, R. C. et al., Bioconductor: open software development for computational biology and bioinformatics. *Genome biology* 5 (10), R80 (2004).

8 Olshen, A. B., Venkatraman, E. S., Lucito, R., & Wigler, M., Circular binary segmentation for the analysis of array-based DNA copy number data. *Biostatistics* (Oxford, England) 5 (4), 557-572 (2004).

9 Beroukhim, R. et al., Assessing the significance of chromosomal aberrations in cancer: methodology and application to glioma. *Proceedings of the National Academy of Sciences of the United States of America* 104 (50), 20007-20012 (2007).

10 Edgar, R., Domrachev, M., & Lash, A. E., Gene Expression Omnibus: NCBI gene expression and hybridization array data repository. *Nucleic acids research* 30 (1), 207-210 (2002).

11 Benito, M. et al., Adjustment of systematic microarray data biases. *Bioinformatics* (Oxford, England) 20 (1), 105-114 (2004).

12 Herschkowitz, J. I. et al., Identification of conserved gene expression features between murine mammary carcinoma models and human breast tumors. *Genome biology* 8 (5), R76 (2007).

All patents, patent applications and references made herein are hereby incorporated by reference in their entirety for all purposes.

TABLE 1

Therapeutic compounds that show significant subtype-specificity. Each column represents q-values for one ANOVA. Compounds are ranked by the minimum q-value achieved across the three tests.

| Compound | Target | Basal/Claudin-low/Luminal | Basal + Claudin-low/Luminal | ERBB2AMP/not ERBB2AMP | Subtype specificity |
|---|---|---|---|---|---|
| Lapatinib | EGFR, ERBB2 | 7.23E−02 | 3.34E−02 | 2.26E−06 | Luminal/ERBB2AMP |
| Sigma AKT1-2 inh. | AKT1, AKT2 | 1.17E−03 | 2.63E−04 | 1.29E−01 | Luminal |
| GSK2126458 | PIK3C A/B/D/G | 1.27E−03 | 1.27E−03 | 8.67E−02 | Luminal/ERBB2AMP |
| Gefitinib | EGFR | 4.89E−01 | 3.35E−01 | 4.14E−03 | ERBB2AMP |
| BIBW 2992 | EGFR, ERBB2 | 6.93E−01 | 8.08E−01 | 6.39E−03 | ERBB2AMP |
| GSK2119563 | PIK3CA | 2.85E−02 | 8.11E−03 | 8.67E−02 | Luminal/ERBB2AMP |
| Rapamycin | MTOR | 1.45E−02 | 8.11E−03 | 3.84E−01 | Luminal |
| AG1478 | EGFR | 9.34E−01 | 9.34E−01 | 2.60E−02 | ERBB2AMP |
| Etoposide | TOP2A | 3.34E−02 | 5.13E−02 | 8.89E−01 | Claudin-low |
| LBH589 | HDAC | 5.14E−02 | 3.34E−02 | 3.22E−01 | Luminal |
| Vorinostat | HDAC | 7.23E−02 | 3.34E−02 | 6.89E−01 | Luminal |
| Cisplatin | DNA cross-linker | 8.45E−02 | 4.31E−02 | 8.52E−01 | Basal/Claudin-low |
| Fascaplysin | CDK4 | 4.83E−02 | 4.31E−02 | 3.70E−01 | Luminal |
| Docetaxel | TUBB1, BCL2 | 8.67E−02 | 4.83E−02 | 8.44E−01 | Basal/Claudin-low |
| GSK1070916 | AURK B/C | 5.13E−02 | 4.83E−02 | 4.82E−01 | Claudin-low |
| PD173074 | FGFR3 | 5.13E−02 | 3.68E−01 | 5.06E−01 | Claudin-low |
| Trichostatin A | HDAC | 1.22E−01 | 5.13E−02 | 7.10E−01 | Luminal |
| Triciribine | AKT, ZNF217 | 8.67E−02 | 5.91E−02 | 3.56E−01 | Luminal |
| CGC-11047 | Polyamine analogue | 6.51E−02 | 1.25E−01 | 8.08E−01 | Basal |
| Temsirolimus | MTOR | 1.64E−01 | 7.25E−02 | 1.29E−01 | Luminal |
| VX-680 | AURK A/B/C | 2.95E−01 | 4.02E−01 | 7.77E−02 | not ERBB2AMP |
| 17-AAG | HSP90AA1 | 1.83E−01 | 1.10E−01 | 8.67E−02 | ERBB2AMP |
| Erlotinib | EGFR | 9.48E−02 | 2.83E−01 | 2.33E−01 | Basal |

TABLE 2

Transcriptional, genomic and phenotypic characteristics of cell lines in the panel.

| Cell Line | Transcriptional Subtype | Transcriptional Subtype + ERBB 2 Status | Culture Media | Doubling Time (hrs) | PIK3CA (3q26.32) GISTIC Amplification | MYC (8q24.21) GISTIC Amplification |
|---|---|---|---|---|---|---|
| 184A1 | Non-malignant, Basal | Non-malignant, Basal | MEGM [a] | 63 | ND | ND |
| 184B5 | Non-malignant, Basal | Non-malignant, Basal | MEGM [a] | 58 | ND | ND |
| 600MPE | Luminal | Luminal | DMEM + 10% FBS | 101 | No Amp | No Amp |
| AU565 | Luminal | ERBB2AMP | RPMI + 10% FBS | 38 | Low Amp | High Amp |
| BT20 | Basal | Basal | DMEM + 10% FBS | 62 | Low Amp | Low Amp |
| BT474 | Luminal | ERBB2AMP | RPMI + 10% FBS | 91 | Low Amp | Low Amp |
| BT483 | Luminal | Luminal | RPMI + 10% FBS | 141 | Low Amp | Low Amp |
| BT549 | Claudin-low | Claudin-low | RPMI + 10% FBS | 25 | No Amp | Low Amp |
| CAMA1 | Luminal | Luminal | DMEM + 10% FBS | 70 | Low Amp | Low Amp |
| HCC1143 | Basal | Basal | RPMI1640 + 10% FBS | 59 | No Amp | Low Amp |
| HCC1187 | Basal | Basal | RPMI1640 + 10% FBS | 71 | No Amp | Low Amp |
| HCC1395 | Claudin-low | Claudin-low | RPMI1640 + 10% FBS | 84 | No Amp | Low Amp |
| HCC1419 | Luminal | ERBB2AMP | RPMI1640 + 10% FBS | 170 | No Amp | High Amp |
| HCC1428 | Luminal | Luminal | RPMI1640 + 10% FBS | 88 | Low Amp | High Amp |
| HCC1599 | Basal | Basal | RPMI1640 + 10% FBS | ND | Low Amp | High Amp |
| HCC1806 | Basal | Basal | RPMI1640 + 10% FBS | 37 | Low Amp | High Amp |
| HCC1937 | Basal | Basal | RPMI1640 + 10% FBS | 49 | Low Amp | High Amp |
| HCC1954 | Basal | ERBB2AMP | RPMI1640 + 10% FBS | 46 | Low Amp | High Amp |
| HCC202 | Luminal | ERBB2AMP | RPMI1640 + 10% FBS | 201 | Low Amp | Low Amp |
| HCC2185 | Luminal | Luminal | RPMI1640 + 10% FBS | 165 | High Amp | High Amp |
| HCC2218 | Luminal | ERBB2AMP | RPMI1640 + 10% FBS | ND | No Amp | Low Amp |
| HCC3153 | Basal | Basal | RPMI1640 + 10% FBS | 59 | Low Amp | High Amp |
| HCC38 | Claudin-low | Claudin-low | RPMI1640 + 10% FBS | 53 | Low Amp | Low Amp |
| HCC70 | Basal | Basal | RPMI1640 + 10% FBS | 73 | Low Amp | Low Amp |
| HS578T | Claudin-low | Claudin-low | DMEM + 10% FBS | 38 | Low Amp | Low Amp |
| LY2 | Luminal | Luminal | DMEM + 10% FBS | 53 | No Amp | High Amp |
| MCF10A | Non-malignant, Basal | Non-malignant, Basal | DMEM/F12 + 5% HS + IHE + CholeraToxin [b] | 27 | ND | ND |
| MCF10F | Non-malignant, Basal | Non-malignant, Basal | DMEM/F12 + 5% HS + IHE + CholeraToxin [b] | 51 | ND | ND |
| MCF12A | Non-malignant, Basal | Non-malignant, Basal | DMEM/F12 + 5% HS + IHE + CholeraToxin [b] | 33 | ND | ND |
| MCF7 | Luminal | Luminal | DMEM + 10% FBS | 51 | No Amp | High Amp |
| MDAMB134VI | Luminal | Luminal | DMEM + 20% FBS | 107 | ND | ND |

TABLE 2-continued

Transcriptional, genomic and phenotypic characteristics of cell lines in the panel.

| Cell Line | Subtype 1 | Subtype 2 | Medium | Col5 | Col6 | Col7 |
|---|---|---|---|---|---|---|
| MDAMB157 | Claudin-low | Claudin-low | DMEM + 10% FBS | 67 | No Amp | Low Amp |
| MDAMB175VII | Luminal | Luminal | DMEM + 10% FBS | 107 | ND | ND |
| MDAMB231 | Claudin-low | Claudin-low | DMEM + 10% FBS | 25 | No Amp | No Amp |
| MDAMB361 | Luminal | ERBB2AMP | DMEM + 10% FBS | 74 | No Amp | Low Amp |
| MDAMB415 | Luminal | Luminal | DMEM + 10% FBS | 85 | Low Amp | Low Amp |
| MDAMB436 | Claudin-low | Claudin-low | DMEM + 10% FBS | 63 | Low Amp | Low Amp |
| MDAMB453 | Luminal | Luminal | DMEM + 10% FBS | 60 | Low Amp | Low Amp |
| MDAMB468 | Basal | Basal | DMEM + 10% FBS | 52 | No Amp | Low Amp |
| SKBR3 | Luminal | ERBB2AMP | McCoy's + 10% FBS | 56 | Low Amp | High Amp |
| SUM102PT | Basal | Basal | Serum Free Ham's F12 + IHE $^f$ | 115 | No Amp | Low Amp |
| SUM1315MO2 | Claudin-low | Claudin-low | Ham's F12 + 5% FBS + IE $^d$ | 113 | No Amp | Low Amp |
| SUM149PT | Basal | Basal | Ham's F12 + 5% FBS + IH $^c$ | 34 | ND | ND |
| SUM159PT | Claudin-low | Claudin-low | Ham's F12 + 5% FBS + IH $^c$ | 22 | No Amp | High Amp |
| SUM185PE | Luminal | Luminal | Ham's F12 + 5% FBS + IH $^c$ | 93 | No Amp | Low Amp |
| SUM225CWN | Luminal | ERBB2AMP | Ham's F12 + 5% FBS + IH $^c$ | 73 | Low Amp | Low Amp |
| SUM44PE | Luminal | Luminal | Serum Free Ham's F12 + IH $^e$ | 85 | ND | ND |
| SUM52PE | Luminal | Luminal | Ham's F12 + 5% FBS + IH $^c$ | 53 | Low Amp | Low Amp |
| T47D | Luminal | Luminal | RPMI1640 + 10% FBS | 56 | Low Amp | Low Amp |
| UACC812 | Luminal | ERBB2AMP | DMEM + 10% FBS | 99 | No Amp | Low Amp |
| UACC893 | Luminal | Luminal | DMEM + 10% FBS | 153 | ND | ND |
| ZR751 | Luminal | Luminal | RPMI1640 + 10% FBS | 68 | No Amp | Low Amp |
| ZR7530 | Luminal | Luminal | RPMI1640 + 10% FBS | 336 | ND | ND |
| ZR75B | Luminal | Luminal | RPMI1640 + 10% FBS | 63 | No Amp | Low Amp |

| Cell Line | CCND1 (11q13.2) GISTIC Amplification | ERBB2 (17q12) GISTIC Amplification | AURKA (20q13.2) GISTIC Amplification | CDKN2A (9p21.3) GISTIC Deletion | PTEN (10q23.31) GISTIC Deletion | Isogenic cell line pair |
|---|---|---|---|---|---|---|
| 184A1 | ND | ND | ND | ND | ND | na |
| 184B5 | ND | ND | ND | ND | ND | na |
| 600MPE | High Amp | Low Amp | No Amp | Low Del | No Del | na |
| AU565 | No Amp | High Amp | High Amp | Low Del | Low Del | SKBR3 |
| BT20 | No Amp | No Amp | High Amp | High Del | Low Del | na |
| BT474 | Low Amp | High Amp | High Amp | Low Del | No Del | na |
| BT483 | Low Amp | Low Amp | Low Amp | Low Del | Low Del | na |
| BT549 | Low Amp | No Amp | Low Amp | No Del | No Del | na |
| CAMA1 | High Amp | No Amp | Low Amp | No Del | Low Del | na |
| HCC1143 | High Amp | Low Amp | Low Amp | Low Del | No Del | na |
| HCC1187 | Low Amp | No Amp | No Amp | No Del | No Del | na |
| HCC1395 | Low Amp | No Amp | Low Amp | High Del | High Del | na |
| HCC1419 | Low Amp | High Amp | High Amp | Low Del | Low Del | na |
| HCC1428 | Low Amp | No Amp | High Amp | No Del | No Del | na |
| HCC1599 | Low Amp | Low Amp | Low Amp | No Del | No Del | na |
| HCC1806 | Low Amp | No Amp | Low Amp | High Del | No Del | na |
| HCC1937 | Low Amp | No Amp | Low Amp | Low Del | High Del | na |
| HCC1954 | High Amp | High Amp | Low Amp | Low Del | Low Del | na |
| HCC202 | No Amp | High Amp | Low Amp | No Del | No Del | na |
| HCC2185 | Low Amp | No Amp | Low Amp | Low Del | Low Del | na |
| HCC2218 | No Amp | High Amp | Low Amp | No Del | Low Del | na |
| HCC3153 | Low Amp | Low Amp | Low Amp | No Del | High Del | na |
| HCC38 | No Amp | Low Amp | Low Amp | High Del | Low Del | na |
| HCC70 | No Amp | No Amp | Low Amp | No Del | Low Del | na |
| HS578T | No Amp | No Amp | Low Amp | No Del | No Del | na |
| LY2 | Low Amp | No Amp | High Amp | High Del | No Del | MCF7 |
| MCF10A | ND | ND | ND | ND | ND | na |
| MCF10F | ND | ND | ND | ND | ND | na |
| MCF12A | ND | ND | ND | ND | ND | na |
| MCF7 | Low Amp | No Amp | High Amp | High Del | No Del | na |
| MDAMB134VI | ND | ND | ND | ND | ND | na |
| MDAMB157 | No Amp | No Amp | Low Amp | No Del | No Del | na |
| MDAMB175VII | ND | ND | ND | ND | ND | na |
| MDAMB231 | No Amp | No Amp | No Amp | High Del | No Del | na |
| MDAMB361 | High Amp | High Amp | High Amp | Low Del | No Del | na |
| MDAMB415 | High Amp | No Amp | Low Amp | No Del | Low Del | na |
| MDAMB436 | No Amp | No Amp | Low Amp | Low Del | Low Del | na |
| MDAMB453 | High Amp | Low Amp | Low Amp | Low Del | No Del | na |
| MDAMB468 | Low Amp | No Amp | Low Amp | No Del | No Del | na |
| SKBR3 | No Amp | High Amp | High Amp | Low Del | Low Del | na |
| SUM102PT | No Amp | No Amp | No Amp | High Del | No Del | na |

TABLE 2-continued

Transcriptional, genomic and phenotypic characteristics of cell lines in the panel.

| | | | | | | |
|---|---|---|---|---|---|---|
| SUM1315MO2 | No Amp | No Amp | No Amp | High Del | No Del | na |
| SUM149PT | ND | ND | ND | ND | ND | na |
| SUM159PT | No Amp | No Amp | No Amp | Low Del | No Del | na |
| SUM185PE | No Amp | No Amp | Low Amp | Low Del | No Del | na |
| SUM225CWN | Low Amp | High Amp | Low Amp | Low Del | Low Del | na |
| SUM44PE | ND | ND | ND | ND | ND | na |
| SUM52PE | Low Amp | No Amp | No Amp | Low Del | Low Del | na |
| T47D | Low Amp | Low Amp | Low Amp | Low Del | No Del | na |
| UACC812 | Low Amp | High Amp | Low Amp | Low Del | No Del | na |
| UACC893 | ND | ND | ND | ND | ND | na |
| ZR751 | High Amp | No Amp | Low Amp | No Del | No Del | na |
| ZR7530 | ND | ND | ND | ND | ND | na |
| ZR75B | High Amp | No Amp | Low Amp | No Del | No Del | ZR751 |

[a] Clonetics MEBM (no Bi Carbonate) + Insulin(5 ug/ml) + Transferrin(5 ug/ml) + Hydrocortisone(0.5 ug/ml) + EGF(5 ng/ml) + Isoprorternol 10e−5M + Bovine Pituitary Extracts 70 ug/ml) + Sodium Bicarbonate (1.176 bmg/ml)
[b] DMEM/F12 + 5% Horse serum + Insulin (10 ug/ml) + Hydrocortisone (500 ng/ml) + EGF (20 ng/ml) + Cholera Toxin (100 ng/ml)
[c] Ham's F12 + 5% FBS + Insulin (5 ug/ml) + Hydrocortisone (1 ug/ml) + HEPES (10 mM)
[d] Ham's F12 + 5% FBS + Insulin (5 ug/ml) + HEPES (10 mM) + EGF (10 ng/ml)
[e] Ham's F12 + Insulin (5 ug/ml) + HEPES (10 mM) + Hydrocortisone (1 ug/ml) + Ethanolamine(5 mM) + Transferrin (5 ug/ml) + T3 (10 nM) + Sodium Selenite (50 nM) + BSA (0.5 g/L)
[f] Ham's F12 + Insulin (5 ug/ml) + HEPES (10 mM) + Hydrocortisone (1 ug/ml) + Ethanolamine(5 mM) + Transferrin (5 ug/ml) + T3 (10 nM) + Sodium Selenite (50 nM) + BSA (0.5 g/L) + EGF(10 ng/ml)
[g] DMEM/F12 + Insulin (250 ng/ml) + Hydrocortisone (1.4 nM) + Transferrin (10 ng/ml) + Sodium Selenite (2.6 ng/ml) + Estradiol (100 nM) + Prolactin(5 ug/ml) + EGF(10 ng/ml)
ND Not done
na not applicable
While we had no data to assign ERBB2 status, literature suggests UACC893 and ZR7530 are ERBB2 amplified (PMID: 1674877, 688225)

TABLE 5

Subtype associations for all therapeutic compounds.

| Compound | Target | Basal/ Claudin-low/ Luminal (q-val) | Basal + Claudin-low/ Luminal (q-val) | ERBB2AMP/ not ERBB2AMP (q-val) | Basal/ Claudin-low/ Luminal (p-val) | Basal + Claudin-low/ Luminal (p-val) | ERBB2AMP/ not ERBB2AMP (p-val) |
|---|---|---|---|---|---|---|---|
| 17-AAG | HSP90AA1 | 1.83E−01 | 1.10E−01 | 8.67E−02 | 4.54E−02 | 2.02E−02 | 1.36E−02 |
| 5-FdUR | TYMS, DNA, RNA | 7.94E−01 | 5.74E−01 | 9.76E−01 | 5.94E−01 | 3.44E−01 | 9.47E−01 |
| 5-FU | TYMS, DNA, RNA | 3.81E−01 | 3.53E−01 | 3.37E−01 | 1.60E−01 | 1.35E−01 | 1.28E−01 |
| AG1024 | IGF1R | 4.51E−01 | 3.22E−01 | 8.46E−01 | 2.31E−01 | 1.09E−01 | 7.09E−01 |
| AG1478 | EGFR | 9.34E−01 | 9.34E−01 | 2.60E−02 | 8.92E−01 | 8.78E−01 | 1.29E−03 |
| AS-252424 | PIK3CG | 9.34E−01 | 8.79E−01 | 3.87E−01 | 8.73E−01 | 7.71E−01 | 1.67E−01 |
| AZD6244 | MAP2K1, MAP2K2 | 9.34E−01 | 8.03E−01 | 8.46E−01 | 8.57E−01 | 6.12E−01 | 7.06E−01 |
| BEZ235 | PIK3CA | 4.33E−01 | 6.10E−01 | 6.89E−01 | 2.05E−01 | 3.68E−01 | 4.61E−01 |
| BIBW 2992 | EGFR, ERBB2 | 6.93E−01 | 8.08E−01 | 6.39E−03 | 4.74E−01 | 6.19E−01 | 2.02E−04 |
| Bortezomib | PSMD2, PSMB1, PSMB5, PSMB2, PSMD1 | 9.34E−01 | 8.08E−01 | 8.79E−01 | 8.88E−01 | 6.28E−01 | 7.69E−01 |
| Bosutinib | SRC | 3.35E−01 | 1.82E−01 | 3.33E−01 | 1.25E−01 | 4.42E−02 | 1.22E−01 |
| Carboplatin | DNA cross-linker | 3.22E−01 | 1.48E−01 | 5.06E−01 | 1.04E−01 | 3.27E−02 | 2.82E−01 |
| CGC-11047 | Polyamine analogue | 6.51E−02 | 1.25E−01 | 8.08E−01 | 8.21E−03 | 2.47E−02 | 6.48E−01 |
| CGC-11144 | Polyamine analogue | 7.19E−01 | 6.80E−01 | 1.81E−01 | 5.09E−01 | 4.38E−01 | 4.32E−02 |
| Cisplatin | DNA cross-linker | 8.45E−02 | 4.31E−02 | 8.52E−01 | 1.26E−02 | 3.37E−03 | 7.29E−01 |
| CRT-11 | TOP1 | 4.33E−01 | 9.83E−01 | 9.34E−01 | 2.09E−01 | 9.76E−01 | 8.88E−01 |
| Docetaxel | TUBB1, BCL2 | 8.67E−01 | 4.83E−02 | 8.44E−01 | 1.47E−02 | 4.32E−03 | 6.99E−01 |
| Doxorubicin | TOP2A | 8.52E−01 | 7.75E−01 | 5.05E−01 | 7.28E−01 | 5.72E−01 | 2.73E−01 |
| Epirubicin | TOP2A | 8.03E−01 | 8.12E−01 | 8.08E−01 | 6.11E−01 | 6.55E−01 | 6.44E−01 |
| Erlotinib | EGFR | 9.48E−02 | 2.83E−01 | 2.33E−01 | 1.67E−02 | 8.28E−01 | 6.19E−02 |
| Etoposide | TOP2A | 3.34E−01 | 5.13E−02 | 8.89E−01 | 2.38E−03 | 5.77E−03 | 7.96E−01 |
| Fascaplysin | CDK4 | 4.83E−02 | 4.31E−02 | 3.70E−01 | 4.37E−03 | 3.50E−03 | 1.52E−01 |
| Gefitinib | EGFR | 4.89E−01 | 3.35E−01 | 4.14E−03 | 2.62E−01 | 1.24E−01 | 1.12E−04 |
| Geldanamycin | HSP90AA1 | 9.86E−01 | 9.83E−01 | 2.02E−01 | 9.86E−01 | 9.78E−01 | 5.27E−02 |
| Gemcitabine | Pyrimidine animetabolite | 4.00E−01 | 6.20E−01 | 5.05E−01 | 1.80E−01 | 3.85E−01 | 2.75E−01 |
| Glycyl-H-1152 | ROCK2 | 5.53E−01 | 3.53E−01 | 2.78E−01 | 3.26E−01 | 1.37E−01 | 7.71E−02 |
| GSK1059615 | PIK3CA | 2.02E−01 | 1.03E−01 | 1.98E−01 | 5.18E−02 | 2.69E−02 | 5.01E−02 |
| GSK1070916 | AURKB, AURKC | 5.13E−02 | 4.83E−02 | 4.82E−01 | 5.59E−03 | 4.57E−03 | 2.56E−01 |
| GSK1120212 | MAP2K1, MAP2K2 | 6.11E−01 | 3.91E−01 | 9.83E−01 | 3.71E−01 | 1.73E−01 | 9.72E−01 |
| GSK1487371 | PIK3CG | 9.34E−01 | 9.02E−01 | 2.78E−01 | 8.82E−01 | 8.17E−01 | 7.56E−02 |
| GSK1838705 | IGF1R | 6.89E−01 | 4.38E−01 | 5.23E−01 | 4.65E−01 | 2.13E−01 | 3.02E−01 |
| GSK2119563 | PIK3CA | 2.85E−02 | 8.11E−03 | 8.67E−02 | 1.54E−03 | 3.01E−04 | 1.43E−02 |
| GSK2126458 | PIK3CA, PIK3CB, PIK3CD, PIK3CG | 1.27E−03 | 1.27E−03 | 8.67E−02 | 2.87E−05 | 2.41E−05 | 1.43E−02 |
| GSK461364 | PLK1 | 3.21E−01 | 1.54E−01 | 7.87E−01 | 1.01E−01 | 3.53E−02 | 5.85E−01 |
| GSK923295 | CENPE | 4.77E−01 | 3.16E−01 | 4.51E−01 | 2.52E−01 | 9.82E−02 | 2.28E−01 |

TABLE 5-continued

Subtype associations for all therapeutic compounds.

| Compound | Target | Basal/ Claudin-low/ Luminal (q-val) | Basal + Claudin-low/ Luminal (q-val) | ERBB2AMP/ not ERBB2AMP (q-val) | Basal/ Claudin-low/ Luminal (p-val) | Basal + Claudin-low/ Luminal (p-val) | ERBB2AMP/ not ERBB2AMP (p-val) |
|---|---|---|---|---|---|---|---|
| Ibandronate sodium salt | FDPS | 6.16E−01 | 5.06E−01 | 3.25E−01 | 3.80E−01 | 2.85E−01 | 1.14E−01 |
| ICRF-193 | TOP2BA, TOP2AB | 4.33E−01 | 9.77E−01 | 8.08E−01 | 2.09E−01 | 9.55E−01 | 6.33E−01 |
| Ispinesib | Kinesin | 6.93E−01 | 6.16E−01 | 9.76E−01 | 4.71E−01 | 3.80E−01 | 9.50E−01 |
| Ixabepilone | TUBB3 | 2.81E−01 | 1.22E−01 | 3.11E−01 | 7.96E−02 | 2.36E−02 | 9.54E−02 |
| L-779450 | BRAF | 8.89E−01 | 9.34E−01 | 8.08E−01 | 7.97E−01 | 8.87E−01 | 6.35E−01 |
| Lapatinib | EGFR, ERBB2 | 7.23E−02 | 3.34E−02 | 2.26E−06 | 9.59E−03 | 2.29E−03 | 1.02E−08 |
| LBH589 | HDAC | 5.14E−01 | 3.34E−02 | 3.22E−01 | 6.02E−03 | 2.41E−03 | 1.09E−01 |
| Lestaurtinib | FLT3, NTRK1 | 4.00E−01 | 4.13E−01 | 5.41E−01 | 1.79E−01 | 1.93E−01 | 3.14E−01 |
| Methotrexate | DHFR | 5.08E−01 | 9.76E−01 | 3.56E−01 | 2.88E−01 | 9.46E−01 | 1.40E−01 |
| MLN4924 | NAE1 | 7.01E−01 | 4.54E−01 | 9.81E−01 | 4.89E−01 | 2.35E−01 | 9.64E−01 |
| NSC 663284 | CDC25A, CDC25B, CDC25C | 5.53E−01 | 6.48E−01 | 7.64E−01 | 3.25E−01 | 4.09E−01 | 5.50E−01 |
| NU6102 | CDK1, CCNB1 | 4.40E−01 | 5.06E−01 | 2.83E−01 | 2.18E−01 | 2.85E−01 | 8.28E−02 |
| Nutlin 3a | MDM2 | 5.19E−01 | 3.56E−01 | 7.68E−01 | 2.97E−01 | 1.42E−01 | 5.57E−01 |
| Oxaliplatin | DNA cross-linker | 7.00E−01 | 8.12E−01 | 3.89E−01 | 4.86E−01 | 6.59E−01 | 1.70E−01 |
| Oxamflatin | HDAC | 7.22E−01 | 4.69E−01 | 8.79E−01 | 5.14E−01 | 2.45E−01 | 7.72E−01 |
| Paclitaxel | TUBB1, BCL2 | 6.21E−01 | 3.87E−01 | 7.95E−01 | 3.89E−01 | 1.67E−01 | 5.98E−01 |
| PD 98059 | MAP2K1, MAP2K2 | 8.08E−01 | 8.89E−01 | 9.25E−01 | 6.28E−01 | 7.95E−01 | 8.41E−01 |
| PD173074 | FGFR3 | 5.13E−02 | 3.68E−01 | 5.06E−01 | 5.54E−03 | 1.49E−01 | 2.78E−01 |
| Pemetrexed | TYMS, DHFR, GART | 4.44E−01 | 8.08E−01 | 3.70E−01 | 2.22E−01 | 6.42E−01 | 1.53E−01 |
| Purvalanol A | CDK1 | 3.22E−01 | 6.89E−01 | 9.38E−01 | 1.08E−01 | 4.50E−01 | 9.00E−01 |
| Rapamycin | MTOR | 1.45E−02 | 8.11E−03 | 3.84E−01 | 6.52E−04 | 3.29E−04 | 1.63E−01 |
| SB-3CT | MMP2, MMP9 | 6.89E−01 | 6.89E−01 | 9.34E−01 | 4.62E−01 | 4.65E−01 | 8.79E−01 |
| Sigma AKT1-2 inhibitor | AKT1, AKT2 | 1.17E−03 | 2.63E−04 | 1.29E−01 | 1.59E−05 | 2.37E−06 | 2.79E−02 |
| Sorafenib | KDR | 8.79E−01 | 7.24E−01 | 6.58E−01 | 7.56E−01 | 5.18E−01 | 4.18E−01 |
| Sunitinib Malate | KDR | 6.89E−01 | 4.40E−01 | 3.22E−01 | 4.54E−01 | 2.17E−01 | 1.10E−01 |
| Tamoxifen | ESR1 | 2.95E−01 | 1.29E−01 | 8.52E−01 | 8.91E−02 | 2.72E−02 | 7.24E−01 |
| TCS 2312 dihydrochloride | CHEK1 | 3.28E−01 | 4.51E−01 | 5.73E−01 | 1.17E−01 | 2.31E−01 | 3.41E−01 |
| TCS JNK 5a | MAPK9, MAPK10 | 8.24E−01 | 7.75E−01 | 8.89E−01 | 6.72E−01 | 5.71E−01 | 7.91E−01 |
| Temsirolimus | MTOR | 1.64E−01 | 7.25E−02 | 1.29E−01 | 3.84E−02 | 1.01E−02 | 2.77E−02 |
| TGX-221 | PIK3CB | 4.10E−01 | 2.78E−01 | 4.09E−01 | 1.90E−01 | 7.76E−02 | 1.88E−01 |
| Topotecan | TOP1 | 8.30E−01 | 8.08E−01 | 7.71E−01 | 6.80E−01 | 6.45E−01 | 5.62E−01 |
| TPCA-1 | IKBKB | 3.22E−01 | 1.54E−01 | 1.29E−01 | 1.12E−01 | 3.50E−02 | 2.64E−02 |
| Trichostatin A | HDAC | 1.22E−01 | 5.13E−02 | 7.10E−01 | 2.30E−02 | 5.78E−03 | 4.99E−01 |
| Triciribine | AKT, ZNF217 | 8.67E−02 | 5.91E−02 | 3.56E−01 | 1.48E−02 | 7.18E−03 | 1.43E−01 |
| Vinorelbine | TUBB | 3.22E−01 | 3.32E−01 | 9.34E−01 | 1.05E−01 | 1.20E−01 | 8.72E−01 |
| Vorinostat | HDAC | 7.23E−02 | 3.34E−02 | 6.89E−01 | 9.77E−03 | 2.34E−03 | 4.62E−01 |
| VX-680 | AURKA, AURKB, AURKC | 2.95E−01 | 4.02E−01 | 7.77E−02 | 8.80E−02 | 1.83E−01 | 1.12E−02 |
| XRP44X | ELK3 | 8.79E−01 | 6.98E−01 | 9.02E−01 | 7.71E−01 | 4.81E−01 | 8.13E−01 |
| ZM 447439 | AURKA | 8.32E−01 | 6.80E−01 | 8.52E−01 | 6.86E−01 | 4.38E−01 | 7.29E−01 |

The invention claimed is:

1. A method for identifying a breast cancer patient suitable for treatment with an anti-cancer agent, wherein said anti-cancer agent is vorinostat, trichostatin A, erlotinib, fluoruracil and/or GSK1070916, said method comprising:
   (a) obtaining a cell from a breast tissue biopsy sample of said cancer patient;
   (b) measuring (i) the genomic copy number or expression level of a set of target genes in said cell from said sample from the patient to identify the molecular or cellular subtype of the cells in said sample, wherein the set of target genes selected comprising at least ER and PR (ii) the genomic copy numbers or expression level of said genes from the patient with normal copy number or the expression level of the gene in a normal tissue sample or a reference expression level, and (iii) the HER2, Claudin and/or K167 protein levels in said cell from said sample from the patient;
   (c) determining the subtype of said cell subtype, wherein (i) a positive level or an increase in the expression level of the target genes ER and PR indicates the cellular subtype of the cells from said cancer patient is luminal, (ii) a decrease in the expression level of the target genes ER and PR, a decrease in HER2 protein levels, and an increase in Claudin protein levels indicates the cellular subtype of the cells is a basal subtype (ER-/PR-/HER2-Claudin+); (iii) a decrease in Claudin protein levels indicates the cellular subtype of the cells is a Claudin low subtype; and (iv) an increase in K167 protein levels indicates the cellular subtype of the cells is K167+ subtype; and
   (d) assigning the patient as suitable for treatment with one of the selected anti-cancer agents based upon the molecular or cellular subtype identified, wherein if the subtype is (i) ER+/PR+, then the patient is assigned as suitable for treatment with Vorinostat and/or Trichostatin A; (ii) luminal, then the patient is assigned as suitable for treatment with Vorinostat and/or Trichostatin A; (iii) basal, then the patient is assigned as suitable for treatment with Erlotinib and/or Fluoruracil, (iv) Claudin-low, then the patient is assigned as suitable for treatment with GSK1070916 and/or Fluoruracil; (v)

K167+, then the patient is suitable for treatment with Fluorouracil and wherein negative or low levels or a decrease in the protein levels of ER, PR, and HER2 and positive levels or an increase in protein levels of Claudin indicates the patient has a basal subtype and is ER-/PR-/HER2-Claudin+, then the patient is assigned as suitable for treatment with Erlotinib and/or Fluoruracil; and (e) administering to said patient a therapeutically effective amount of one of the anti-cancer agents, Vorinostat, Trichostatin A, Erlotinib, Fluoruracil or GSK1070916.

2. The method of claim 1, wherein step b) further comprises measuring 20q13 amplification levels in said cell from said sample of the patient, and wherein if the subtype is low or no 20q13 amplification is measured, then the patient is assigned as suitable for treatment with GSK1070916.

* * * * *